(12) United States Patent
Makiyama et al.

(10) Patent No.: US 10,709,923 B2
(45) Date of Patent: Jul. 14, 2020

(54) APPARATUS FOR MOTOR REHABILITATION OF UPPER AND LOWER LIMBS

(71) Applicants: Antonio Massato Makiyama, São Paulo (BR); Tomas Yoshio Makiyama, São Paulo (BR)

(72) Inventors: Antonio Massato Makiyama, São Paulo (BR); Tomas Yoshio Makiyama, São Paulo (BR)

(*) Notice: Subject to any disclaimer, the term of this patent is extended or adjusted under 35 U.S.C. 154(b) by 196 days.

(21) Appl. No.: 15/715,211

(22) Filed: Sep. 26, 2017

(65) Prior Publication Data
US 2018/0085616 A1 Mar. 29, 2018

(30) Foreign Application Priority Data

Sep. 26, 2016 (BR) .............................. 102016022139

(51) Int. Cl.
*A63B 21/005* (2006.01)
*A61H 1/02* (2006.01)
(Continued)

(52) U.S. Cl.
CPC .......... *A63B 21/0058* (2013.01); *A41B 11/00* (2013.01); *A41D 19/00* (2013.01);
(Continued)

(58) Field of Classification Search
CPC ............ A63B 21/0058; A63B 21/4034; A63B 21/4035; A63B 21/4049; A63B 21/00178;
(Continued)

(56) References Cited

U.S. PATENT DOCUMENTS 5,466,213 A 11/1995 Hogan et al.
5,704,881 A 1/1998 Dudley
(Continued)

FOREIGN PATENT DOCUMENTS

BR PI1000960-4 A2 4/2011
JP H01316815 A 12/1989
(Continued)

OTHER PUBLICATIONS

European Search Report in corresponding Application No. 17193334.4, dated Feb. 21, 2018, 6 pages.

*Primary Examiner* — Sundhara M Ganesan
(74) *Attorney, Agent, or Firm* — Kintner IP, LLC; Mary Frances Ludwig

(57) ABSTRACT

An apparatus for the motor rehabilitation of the upper and lower limbs is disclosed, which is compact, portable, lightweight, and easy to transport. The apparatus has an adapter for the distal end of the patient's limb, a robotic arm, a gear system, two motors, and virtual and/or augmented reality software to interact with the patient. A management and control system makes possible the execution of movements and exercises in the three-dimensional space so that patients with neurological, musculoskeletal, muscular, rheumatic, motor and/or cognitive diseases or injuries and patients in post-surgical recovery may exercise and recover the movements of their upper and/or lower limbs. The equipment may also be used for the purpose of training and physical fitness.

30 Claims, 24 Drawing Sheets

(51) Int. Cl.
| | | |
|---|---|---|
| G16H 20/30 | (2018.01) | |
| G16H 40/63 | (2018.01) | |
| A63F 13/24 | (2014.01) | |
| A63F 13/42 | (2014.01) | |
| A63F 13/212 | (2014.01) | |
| A63F 13/285 | (2014.01) | |
| A63F 13/85 | (2014.01) | |
| A63B 21/00 | (2006.01) | |
| A41B 11/00 | (2006.01) | |
| A41D 19/00 | (2006.01) | |
| A63B 23/035 | (2006.01) | |
| A63B 24/00 | (2006.01) | |
| A63B 71/06 | (2006.01) | |
| G06T 19/00 | (2011.01) | |

(52) U.S. Cl.
CPC .......... *A61H 1/024* (2013.01); *A61H 1/0237* (2013.01); *A61H 1/0244* (2013.01); *A61H 1/0274* (2013.01); *A61H 1/0277* (2013.01); *A61H 1/0281* (2013.01); *A61H 1/0285* (2013.01); *A63B 21/00178* (2013.01); *A63B 21/00181* (2013.01); *A63B 21/4034* (2015.10); *A63B 21/4035* (2015.10); *A63B 21/4049* (2015.10); *A63B 23/0355* (2013.01); *A63B 24/0087* (2013.01); *A63B 71/0622* (2013.01); *A63F 13/212* (2014.09); *A63F 13/24* (2014.09); *A63F 13/285* (2014.09); *A63F 13/42* (2014.09); *A63F 13/85* (2014.09); *G16H 20/30* (2018.01); *G16H 40/63* (2018.01); *A41B 2400/32* (2013.01); *A61H 2201/0157* (2013.01); *A61H 2201/1215* (2013.01); *A61H 2201/14* (2013.01); *A61H 2201/164* (2013.01); *A61H 2201/165* (2013.01); *A61H 2201/169* (2013.01); *A61H 2201/1638* (2013.01); *A61H 2201/1642* (2013.01); *A61H 2201/1659* (2013.01); *A61H 2201/1673* (2013.01); *A61H 2201/1685* (2013.01); *A61H 2201/5007* (2013.01); *A61H 2201/5035* (2013.01); *A61H 2201/5043* (2013.01); *A61H 2201/5058* (2013.01); *A61H 2201/5061* (2013.01); *A61H 2201/5079* (2013.01); *A61H 2205/06* (2013.01); *A61H 2205/062* (2013.01); *A61H 2205/065* (2013.01); *A61H 2205/088* (2013.01); *A61H 2205/10* (2013.01); *A61H 2205/102* (2013.01); *A61H 2205/12* (2013.01); *A63B 2071/0666* (2013.01); *A63B 2209/00* (2013.01); *A63B 2209/10* (2013.01); *G06T 19/006* (2013.01)

(58) Field of Classification Search
CPC .......... A63B 21/00181; A63B 23/0355; A63B 24/0087; A63B 71/0622; A63B 2071/0666; A63B 2209/00; A63B 2209/10; A63B 23/035; A61H 1/0237; A61H 1/024; A61H 1/0244; A61H 1/0277; A61H 1/0281; A61H 1/0285; A61H 2201/164; A61H 2201/5035; A61H 2201/5061; A61H 2201/5007; A61H 2201/1659; A61H 2201/5043; A61H 2205/12; A61H 2201/14; A61H 2201/5058; A61H 2201/5079; A61H 2205/06; A61H 2205/10; A61H 2201/1215; A61H 2201/1638; A61H 2201/1642; A61H 2201/165; A61H 2201/1673; A61H 2201/1685; A61H 2201/169; A61H 2205/062; A61H 2205/065; A61H 2205/088; A61H 2205/102; A61H 1/00; A61H 2201/1666; A61H 1/0218; A61H 2201/1207; G16H 20/30; G16H 40/63; A63F 13/24; A63F 13/42; A63F 13/212; A63F 13/285; A63F 13/85; A63F 13/245; A41B 11/00; A41B 2400/32; A41D 19/00; G06T 19/006; G06F 3/0383
See application file for complete search history.

(56) References Cited

U.S. PATENT DOCUMENTS

| | | |
|---|---|---|
| 5,951,499 A | 9/1999 | Saringer et al. |
| 6,666,831 B1 | 12/2003 | Edgerton et al. |
| 7,367,958 B2 | 5/2008 | McBean et al. |
| 7,618,381 B2 | 11/2009 | Krebs et al. |
| 8,177,688 B2 | 5/2012 | Burnfield et al. |
| 2006/0106326 A1* | 5/2006 | Krebs .................. A61H 1/0274 601/40 |
| 2007/0282228 A1* | 12/2007 | Einav .................. G06F 19/00 601/33 |
| 2015/0342817 A1 | 12/2015 | Gu et al. |
| 2016/0000633 A1 | 1/2016 | An et al. |

FOREIGN PATENT DOCUMENTS

| | | |
|---|---|---|
| JP | 2002127058 A | 5/2002 |
| WO | WO/2005/074371 A2 | 8/2005 |
| WO | WO/2006/082584 A2 | 8/2006 |
| WO | 2012176200 A1 | 12/2012 |
| WO | 2014057410 A1 | 4/2014 |
| WO | 2014/085810 A1 | 6/2014 |

* cited by examiner

APPARATUS FOR MOTOR REHABILITATION OF UPPER AND LOWER LIMBS

CROSS REFERENCE TO RELATED APPLICATION

This application claims foreign priority under 35 U.S.C. § 119(a)-(d) to Patent Application No. BR 102016022139-0, filed in Brazil on 26 Sep. 2016, which is hereby incorporated by reference.

TECHNICAL FIELD

The present invention pertains generally to systems for physical therapy, and more particularly to an apparatus for motor rehabilitation of the upper and lower limbs.

BACKGROUND OF THE INVENTION

Neurological, musculoskeletal, muscular, rheumatic, motor and/or cognitive diseases or injuries can cause great disruption in people's lives, incapacitating them from their daily activities, from simpler activities such as picking up an object, to more complex activities such as personal care and hygiene and handling equipment. Such diseases and injuries may impair a person's ability to function in everyday life.

In addition to injuries due to accidents, physical trauma, and degenerative diseases or strokes (CVA, cerebrovascular accidents), motor rehabilitation may also be necessary after surgeries, so that the patient may resume his/her regular activities.

To help patients' recovery, there is the one-on-one work of physiotherapists, who perform individual exercises for each patient, by using techniques developed in this field of human knowledge.

Although the work of these professionals may be important for patient rehabilitation, treatment, and recovery, physiotherapy sessions are usually time intensive, requiring the physiotherapist's physical participation, since he is executing the exercises along with the patient. With this, the patient's exercise time is limited to the duration of the session with the physiotherapist. Moreover, the exercises require the physiotherapist's own physical exertion, which will affect the quality of treatment. The physiotherapist, fatigued after several sessions, will not have the strength to execute exercises and movements in a consistent way with all patients.

Another disadvantage faced by the physiotherapist is that his ability to evaluate a patient's force, capacity of movement, and progress is highly subjective. In other words, where an evaluation or quantitative monitoring with objective numerical data is not possible, the result may be an inaccurate diagnosis and the prescription of insufficient treatment for a specific patient. Moreover, due to the subjectivity of the evaluation and monitoring, two or more physiotherapists may have diverging opinions.

In the attempt to aid a patient's motor rehabilitation and the physiotherapist's work, various types of equipment have been developed for motor rehabilitation of the upper and/or lower limbs, which are discussed below.

U.S. Pat. No. 8,177,688, for example, shows a large-size apparatus for the rehabilitation of lower limbs. It requires particular installations for its operation, which are difficult to transport and require the patient to remain standing while performing the exercises. Depending on the degree of the injury, it may even be necessary for the patient to be supported by straps, cords, and other devices.

U.S. Pat. No. 5,704,881 shows another large-size rehabilitation equipment where the patient is suspended by a set of cables.

U.S. Pat. No. 6,666,831 also shows a large-size equipment for the rehabilitation of lower limbs in which the patient is suspended by cables connected to his/her trunk, while each leg is connected to two mechanical rods that lift and lower the legs.

US Pat. App. No. 2015/0342817 shows a rehabilitation equipment for the lower limbs, which executes movements on the horizontal plane. In order to achieve the patient's rehabilitation the lower limb is positioned on a support.

Brazilian Patent PI 1000960-4 shows a rehabilitation equipment for the lower limbs in which the patient is suspended through cables and the lower limbs are moved upward and downward to reach motor rehabilitation.

Pat. App. Pub. WO 2014/085810 shows an apparatus for hand rehabilitation, which uses a spring system, pinion and rack gears and a motor to perform pronation and supination exercises or flexion and extension, one at a time, on a horizontal plane.

U.S. Pat. No. 7,367,958 shows an orthosis with an electromyographic sensor that is connected to the patient's arm and forearm, which is designed to stimulate the movement of the upper limb.

U.S. Pat. No. 5,951,499 shows an apparatus for the rehabilitation of the arm, forearm and hand, which performs only pronation and supination movements in the limb and takes a long time for the accommodation of the upper limb in the apparatus.

US Pat. App. No. 2016/0000633 shows a rehabilitation equipment that can execute exercises, one at a time, on a two-dimensional plane, by employing actuators, articulated arms, and a system that permits the movement of articulated arms to perform the rehabilitation exercises.

U.S. Pat. No. 5,466,213 shows a larger size apparatus directed toward the rehabilitation of the upper limbs composed of articulated arms that permit the execution of exercises, one at a time, on the two-dimensional plane. By this apparatus, the patient can perform separately flexion and extension exercises, after pronation and supination exercises, in addition to exercises with lateral movements. The size of the apparatus makes it difficult to transport.

U.S. Pat. No. 7,618,381 shows a rehabilitation apparatus for upper limbs that works with the patient's forearm and wrist set on a support or apparatus for the execution of exercises for the wrist. These exercises are performed on a two-dimensional plane. The part of the apparatus that exercises the wrist has three motors to perform its work and is connected to articulated arms linked to two motors for the execution of exercises for the rest of the upper limb, such that the patient's arm is also set on a support. Due to its characteristics, the apparatus has dimensions that make its transport difficult. The positioning of the patient's limb in the equipment takes a long time and the movements of the limbs are in the horizontal plane and with a support, performed one at a time.

Pat. App. Pub. WO 2014/057410 presents an exoskeleton for the rehabilitation and movement of lower limbs.

Pat. App. Pub. WO 2012/176200 shows a rehabilitation apparatus for the upper limbs which contains a sensor system, a mechanism of actuators and a data processing module to capture information about the healthy limb and to generate exercises for the member that requires rehabilitation.

Although the above may represent an advance in the motor rehabilitation of patients' upper or lower limbs, these apparatuses which represent the current state of the technology suffer from inconveniences and other disadvantages.

One of the disadvantages regards the size of the rehabilitation apparatuses, which have a large size, are difficult to be transported and need special locations to be prepared for their installation and their use. With such apparatuses, the patient must go to a facility where the apparatus is installed and therefore the execution of exercises is limited to the availability of this particular location's schedule, restricting the number of exercises that the patient can perform and increasing his/her time of recovery.

Another disadvantage is related to the time needed to position the patient's limb in the apparatus. As most apparatuses require the limb to be set on a support or device or the patient to be suspended by cables, a considerable time of the physiotherapy session is spent on the patient's positioning, which reduces the time of the exercises of the rehabilitation session.

It should be stated that the movements and exercises enabled by these apparatuses of the current state of the technology do not resemble the movements performed in daily life activities. This is because, during the exercises and movements, the patient's limb rests upon supports and devices or the patient is suspended by cables, which typically does not resemble daily life situations. Under normal conditions, people execute predominantly curvilinear movements in three-dimensional space.

These apparatuses are designed to perform the exercises one at a time without any integration of the movements, which, again, is dissimilar to movements that people perform in daily life.

Another disadvantage of the apparatuses of the current state of the technology is that they are made to perform exercises only on a horizontal plane, which generates a partial stimulus of the brain. This is because in the movement on a horizontal plane the force of gravity, which has vertical orientation and downward direction, does not influence the movement of the limb. This partial stimulation results in a longer and less effective rehabilitation for the patient.

A small amount of equipment pertaining to the current state of the technology uses software programs integrated to the apparatus in order to interact with the patient during the execution of exercises. These software programs, however, do not sufficiently stimulate and motivate the patient because they only show the point of origin and the point of destination of the movement, without any virtual setting to contextualize the exercises and movements in the patient's daily life and without creating links and similarities to the person's daily life activities. Aside from this, the current software programs are not entertaining and do not have an auditory and visual design conducive to the patient's cognitive stimulation during the rehabilitation sessions.

The invention that is the object of this patent application was developed in a new, original and creative way to help in the motor rehabilitation of the upper and lower limbs, by employing an innovative solution, which extends the current knowledge and incorporates significant innovations in this field of human knowledge.

This apparatus can be used by patients with neurological, musculoskeletal, muscular, rheumatic, motor and/or cognitive diseases or injuries, such as patients who have suffered CVA (cerebrovascular accident or stroke) or who are in a more advanced stage of Parkinson's or Alzheimer's diseases or who have suffered accidents or physical traumas. It may also be used for patients in recovery after a surgery, for patients who are trying to correct or to learn movements again, and for preventative training designed to prevent the progression of these diseases.

BRIEF SUMMARY OF THE INVENTION

The present invention refers to an apparatus for the motor rehabilitation of the upper and lower limbs, which is compact, portable, lightweight, and easy to transport. The apparatus has an adapter for the distal end of the patient's limb, a robotic arm, a gear system, two motors, and a virtual and/or augmented reality software to interact with the patient. A management and control system makes possible the execution of movements and exercises in the three-dimensional space so that patients with neurological, musculoskeletal, muscular, rheumatic, motor and/or cognitive diseases or injuries and patients in post-surgical recovery may exercise and recover the movements of their upper and/or lower limbs. Apart from its use in motor rehabilitation, the apparatus may also be used for the purposes of training and physical fitness.

The apparatus works with movements and exercises in the three-dimensional space and provides excellent conditions so that the patient may perform movements very similar to those that he/she would perform in his/her daily life activities. Without the desire of being exhaustive, some examples of these activities would include: moving objects from one place to another, picking up an object and placing it on a table, moving tableware and food to the mouth, opening a door, serving breakfast, collecting fruits, picking up bread and placing it in an oven or a microwave oven, kicking a ball, accelerating an automobile, going up stairs, physical activities, physical fitness exercises, and playing games, among others.

These movements are in the three-dimensional space. For example, reaching movements, cross movements, ipsilateral movements and contralateral movements, require greater muscular activation, especially when compared with movements performed on the horizontal plane and with a support to the limb, and promote a greater stimulus of the brain, because it will be necessary to move a greater number of muscular groups and the brain is required to recruit a higher number of neural circuits to execute the exercise.

The way by which the limb is connected to the apparatus causes it to be suspended in the space and the movement is under the influence of gravity, which makes the exercise very similar to the movements of daily life. It increases muscle effort and cerebral work to coordinate these movements, which leads to the acceleration of the rehabilitation process.

It should also be mentioned that the movements performed in the person's daily life activities have predominantly curvilinear trajectories, which is reproduced by and exercised with the present apparatus.

With these characteristics, the apparatus provides a faster and more effective rehabilitation. It exceeds in many aspects the abilities of the currently available equipment, which work only on the horizontal plane and with the limb moving with the aid of a support. These deficiencies in current equipment cause a reduced stimulus of the brain and also produce exercises that are dissimilar to daily life activities.

In the present apparatus, in the active mode, the patient moves the end of the robotic arm while this movement is shown on the screen.

In the active-assistive mode, the apparatus helps in the execution of the movements, modulating the forces, displacements, velocities and accelerations in accordance with the individual patient's needs and according his/her rehabilitation plan. This is very useful, for example, for the motor rehabilitation of patients with stroke (CVA, cerebrovascular accident), which have irregular movements of the limb. The apparatus is able to follow and correct gently the deviations of movements, in order to maintain them within the desired trajectory.

In the active-assistive mode it is also possible to program the apparatus to offer resistance to the patient's movement, which is particularly useful for training and physical fitness exercises.

In the passive mode, the apparatus guides the patient limb's movements in accordance with the established rehabilitation plan.

These trajectories involve therapeutically functional movements and exercises with displacements, velocities and accelerations according to the prescribed rehabilitation treatment for the patient or according to the training and physical fitness plan.

Aside from these applications, the apparatus can be used to evaluate, monitor and diagnose the patient's motor problems and his/her recovery. This is done by measuring the force, spatial trajectory, velocity, accuracy and other diagnostic and follow-up variables, in other words, by obtaining accurate and objective numerical data for a more careful evaluation and for the establishment of a more effective and faster rehabilitation plan.

Given that the apparatus is compact, portable, lightweight, easy to transport, and does not require facilities exclusively adapted to its use, it can be used at the patient's home, in rehabilitation clinics, physiotherapy clinics, medical clinics, hospitals and even in sport centers for training and physical fitness.

The present apparatus has an adapter for connecting the distal end of the patient's upper or lower limb, a robotic arm, a gear system, two motors, one or two drivers, a virtual and/or augmented reality software and a management and control system.

The adapter which allows the connection of the distal end of the patient's limb to the motor rehabilitation apparatus can be configured in various ways, depending on whether it is connected to the patient's hand or foot, on the type of exercise that is desired, and on the type of sequela the patient has developed.

For upper limb rehabilitation, the adapter for the connection with the hand would preferably have the shape of a sphere or an anatomical shape for the patient's fingers or hand, but also it is possible to employ a handle, a joystick or other form that ensures a comfortable grip.

Inside, the adapter can contain sensors so that the patient may press it with the hand or foot to obtain visual, sound or other type of effects on the screen of the virtual and/or augmented reality software, which generates an even greater stimulus to the patient because the cognitive function of the brain is also exercised together with the motor system.

For lower limb rehabilitation, the adapter may have the shape of a sphere, an ellipsoidal, a plate, a pedal or some other form that ensures the comfortable positioning of the foot.

In both cases, the connection of the hand and foot with the adapter is done preferably with a glove or sock, or tapes and straps with hook and loop fasteners, which aims at reducing the time needed to connect the patient to the apparatus. For this activity, it is enough to position the hand and foot in the adapter and to use the glove or sock, and affix the tape or strap with fasteners, which simplifies and speeds up the work, leaving more time for the execution of exercises.

The adapter will be made preferably of silicon, but plastics, polymers, elastomers, foams, woods, metals or other materials can be employed presenting or not superficial coverings, textures or relieves that may facilitate the connection with the patient or stimulate tactile aspects or sensitivity of the limb's end.

The adapter can be fixed on the robotic arm or can contain inside it a universal joint, a bearing system or a spherical joint to allow mobility in relation to the robotic arm.

Preferably the bearing system, the universal joint or spherical joint will be used because the rotational movement of the adapter in relation to the robotic arm allows the execution of more combined movements of the wrist and the patient's limb, which enhances recovery and brings more versatility to the apparatus.

For example, in the rehabilitation of an upper limb, the use of the bearing system or a universal joint or spherical joint allows the patient to make the rotation of the wrist in combination with the exercises for the forearm, arm and shoulder. In the case of the rehabilitation of a lower limb, the ankle can have rotational movements together with the movements for the knee, leg and hip.

It is should be emphasized that, in the apparatus, the only point of connection between the patient's limb with the apparatus is made through this adapter. By this means, the patient's entire limb is suspended in space, without any support or supporting apparatus, under the action of gravity and free to move in the three-dimensional space, which allows the rehabilitation exercises and movements to more closely approximate movements that the person performs in daily life.

Aside from this, this form of connection together with the movements in the three-dimensional space makes the exercises more complex, provides the execution of integrated and simultaneous exercises for all parts and joints of the limb, requires a greater effort of the patient's musculature, provides a greater stimulus of the brain and allows the execution of movements with curvilinear trajectory, which benefits the patient and speeds up his/her motor rehabilitation.

In the case of training and physical fitness exercises, it is possible to regulate the quantity or require specific muscular efforts for the movements, leading to faster and more effective results.

The robotic arm is composed preferably of a larger rod, with length varying between about 1 cm and about 100 cm, and a smaller rod, with length between about 5 cm and about 50 cm, such that the union of these two rods can form any angle between each other.

The rods can be straight or may have some kind of curvature, such that the robotic arm can be compatible only with the smaller rod, whether straight or with some curvature and with length between about 5 cm and about 100 cm.

The robotic arm can be made of metal, plastic, wood, polymer or other type of material, presenting or not superficial coverings, relieves or textures.

The core of the arm can also be manufactured with these materials and applied a superficial covering or a finishing material or relieves or textures with the mentioned materials. In a preferred configuration the robotic arm has a metal core and a plastic covering.

At one end, the robotic arm is connected to the adapter for the patient's hand or foot and, on the other, it is connected to a gear system, with satellite arrangement, such that its fixation to the gear system is done through screws, pins, adhesives, glue or other fixation element.

The gear system is composed of two opposing gears, a spider gear and a connection element that is positioned between them.

The opposing gears are connected to the motors through semi-axles and/or bushings, while the spider gear is connected to the robotic arm and is in a perpendicular position to the opposing gears.

The gears are conic or semi-spherical, may have straight or helical teeth and may or may not have a mechanism to prevent clearances or backlash.

The connection element between the gears may have the shape of a polygonal or circular base prism, of a sphere or a polyhedron.

This connection element is connected to the spider gear through a pin and is in contact with the opposing gears. The connection element will be responsible for maintaining the connection between the three gears.

The motors transmit torques and rotations to the opposing gears, which, in turn, produce the movement of the spider gear, which will generate the movement of the robotic arm, resulting in the displacement of the patient's limb through the three-dimensional space for a given trajectory, velocity and acceleration. It should be emphasized that these movements will be very similar to those that are executed by healthy people in daily life activities.

To exemplify the operation of the gear system and its result in the movement of the robotic arm, we can mention, without the intention of being exhaustive, some types of rotations of the gears.

In the case of two opposing gears having rotations in the same direction around a common axis and with the same magnitude, the connection element and the spider gear will trace a curvilinear movement on a plane perpendicular to the horizontal axis of the opposing gears, causing the robotic arm and the patient's limb to trace this type of movement on this same perpendicular plane.

In the case of an upper limb, the hand, forearm, arm and shoulder will perform a flexion and extension exercise. Supposing that the adapter for connecting the hand has the bearing system or universal joint or spherical joint, the wrist will execute a rotational movement in conjunction with the flexion and extension movement of the rest of the limb.

If the exercise is applied on a lower limb, the flexion and extension movement will occur on the foot, leg, thigh and hip, such that the ankle will still execute a rotational movement.

In the case of two opposing gears having rotations in opposite directions around a common axis, but with the same magnitude, the spider gear will rotate around its own central axis, the connection element will stay in the same position and the robotic arm will trace a movement with curvilinear trajectory on a plane perpendicular to the central axis of the spider gear.

Consequently, in the case of an upper limb, the limb will move in a curvilinear trajectory on a perpendicular plane, which will generate combined and integrated exercises for the limb's joints and muscles. In the case of a lower limb, there will be eversion and inversion of the foot; extension and flexion of the ankle joint; flexion, extension and rotation of the knee, because the patient is seated and the knee is found to be in flexion for the execution of the exercise.

On the hypothesis that the opposing gears have rotations with different magnitudes, whether with the same or opposite directions, or even in cases where an opposing gear is rotating and the other opposing gear does not move, we will have movements of the connection element and the spider gear on oblique planes in relation to the horizontal plane producing, in the robotic arm and on the patient's upper limb, movements with curvilinear oblique trajectories in the three-dimensional space, which could execute, in the course of this trajectory, reaching movements, cross movements, ipsilateral movements, contralateral movements, pronation and supination, flexion and extension, adduction and abduction. For the lower limb, the movements are analogous, except for the pronation and supination, which correspond to internal and external rotation of the knee. These movements require greater muscular activation and greater stimulus for the brain because it will be necessary to move a greater number of muscular groups and the brain will have to recruit a higher number of neural circuits to perform the exercise, providing the patient with a faster and more effective rehabilitation.

Thus, it is possible to verify that the movements of the gears will generate a large variety of trajectories in the three-dimensional space, allowing the execution of various movements and rehabilitation exercises and also training and physical fitness exercises.

An important distinctive characteristic of the invented apparatus is that the exercises applied to the patient's limbs are integrated. They exercise various muscular groups at the same time; they are performed under effect of the force of gravity; and they describe curvilinear trajectories in the three-dimensional space, which is much closer to the movements made in daily life by healthy people.

Thus, the movement generated by the gear system and the positioning of the suspended limb in space allows for the execution, at the same time, of several functional rehabilitation exercises of the limb, using the trajectory of the end of robotic arm. For example, latero-lateral, cross, ipsilateral, contralateral, eversion and inversion, adduction and abduction, flexion and extension and pronation and supination exercises, which overcomes the pieces of equipment of the current state of the technology, which execute exercises with planar trajectories, done one at a time and with the patient's limb positioned on supports.

Each opposing gear is connected to a motor through a semi-axle and/or a bushing and there may or may not be a gear reduction box between the opposing gear and the motor.

The motors have a torque between about 0.05 Nm and about 50 Nm and have position sensors that will transmit information to the management and control system.

The motors can be aligned with the respective opposing gears or can be positioned perpendicularly to them, such that, in this case, the transmission of the movement from the motor to the gear will use a connector or an "L"-shaped gear reduction box.

In the preferred configuration of the invented apparatus, each motor is connected to a driver, which is a converter of logical signals into electrical signals, and there is a connection between the two drivers of the apparatus for data synchronization. However, it is possible to have only one driver, serving the two motors.

The driver receives the logical signals coming from the management and control system and converts these logical signals into electrical signals which will be sent to the motors to generate the rotations and torques.

The management and control system receives information from the virtual and/or augmented reality software and manages and controls in real time the data transmissions between the virtual and/or augmented reality software, the drivers and the motors, by controlling the movement of the gears, the robotic arm and the patient's limb interactively.

The virtual and/or augmented reality software makes the visual interaction with the patient and contains the information and data of movements that will be applied in the motor rehabilitation exercises or in training and physical fitness exercises.

With the data received from the virtual and/or augmented reality software, the management and control system calculates the trajectory to be performed by the patient, together with the force and acceleration of the movement, and sends logical signals to the drivers, which will convert them into electrical signals that will move the motors, producing the rotations and torques in the gears. As a result, they will have the movements of the gears, the robotic arm and the patient's limb in a given trajectory, with certain force and acceleration.

At the same time that it sends data, the management and control system receives feedback with information on the patient's movements, compares them with the information received from the virtual and/or augmented reality software, recalculates the trajectories and sends the signals to the motors to produce rotations and torques to correct the trajectory, the force and the acceleration of the patient's movement. At the same time, it transmits this information to the virtual and/or augmented reality software to show the corrections of the movement on the screen or on the monitor.

The virtual and/or augmented reality software, which interacts with the patient, has a friendly, entertaining and motivating graphical interface. It has games, various scenarios and environments with figures, colors and sounds to simulate people's daily life situations, such as carrying an object from one point to another, picking up an object on a shelf and placing it on a table, opening a door, serving breakfast, picking up a fruit from the fruit basket and placing it on the plate, collecting a fruit, picking up bread and placing in an oven or microwave oven, performing physical activities and physical fitness exercises, playing games, accelerating a car, kicking a ball, going up stairs, among other situations.

In all these situations, the three-dimensional figure of the patient's hand or foot always appears on the screen or on the monitor, simulating in this manner the corresponding functional movements of the limbs so that he/she may evoke in his/her imagination the dynamics of the reality of that situation, using the affected limb during the therapy, and thus activating and rehabilitating the injured cerebral area corresponding to the movement.

The virtual and/or augmented reality software shows the movements of the end of the robotic arm, which corresponds to the patient's hand or foot, placing these movements in virtual scenarios or games so that the patient may feel integrated into the virtual environment and may have the view of the hand or foot movement trajectory in three-dimensional space and a motivation to perform the movement.

This interaction between the apparatus and the patient, through the virtual and/or augmented reality software, is very important for the motor rehabilitation process because the patient can have a visual feedback of the movement of his/her limbs in an entertaining manner and that simulates the reality; he/she can feel the force that the apparatus makes on the limb and also the corrections of position, trajectory, force and acceleration when the movement in the three-dimensional space is different from what is planned for the rehabilitation exercise and for the physical fitness exercise.

An improvement and rehabilitation occur not only to the patient's motor and muscular system but also to his/her cognitive function.

The virtual and/or augmented reality software can be displayed on a television screen, on a computer monitor, on a projector or through any media that allows the visualization by the patient.

The virtual and/or augmented reality software, with its games and virtual scenarios, can operate without any additional part, but to improve the patient's immersion into the game or virtual scenario and to expand cognitive stimuli, the use of virtual and/or augmented reality glasses is possible.

The invented apparatus has video ports in the standard market formats, such as VGA, HDMI and/or DVI.

Another characteristic of the virtual and/or augmented reality software is that it can be multiplayer. Two or more patients using different pieces of apparatus can interact in the same game, environment or virtual reality scenario, which makes the exercises even more similar to those that are performed by healthy people in their daily life activities.

The virtual and/or augmented reality software can be programmed for each patient's specific needs and, after this programming, the patient is able to perform his/her exercises without the need of the individual supervision of a physiotherapist.

The invented apparatus is compact, portable, lightweight and easy to transport. The patient can perform exercises at home as many times as he/she can or wishes, which speeds up his/her rehabilitation or the training and the physical fitness process.

This also facilitates the physiotherapist's work because it allows him to attend to and supervise the exercises of various patients at the same time, whether at the place where the pieces of apparatus are or even remotely.

Each patient's exercise plan is stored in the virtual and/or augmented reality software and it can be accessed by a password or through biometric controls.

The apparatus also has a touchscreen device, like a tablet, or other external devices, such as a keyboard and mouse, for access to the apparatus's control functions. With this, the physiotherapist or the patient can access the parameters of the rehabilitation or physical fitness exercises.

Other embodiments, in addition to the embodiments enumerated above, will become apparent from the following detailed description, taken in conjunction with the accompanying drawings, which illustrate, by way of example, the principles of the apparatus and method of use.

DETAILED DESCRIPTION OF THE INVENTION

Figure 1:
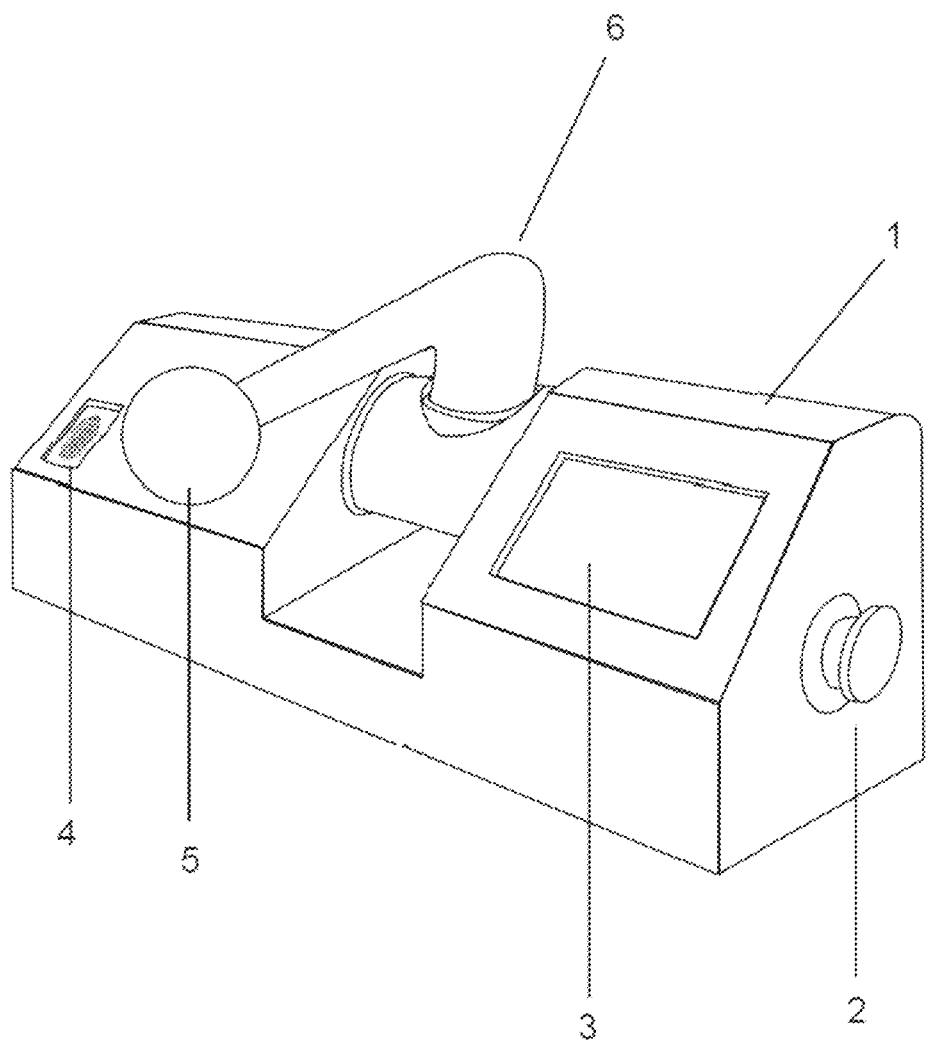
FIG. 1 shows a perspective view of a motor rehabilitation apparatus for the upper and lower limbs, having a sphere-shaped adapter for the end of the upper limb.
Figure 2:
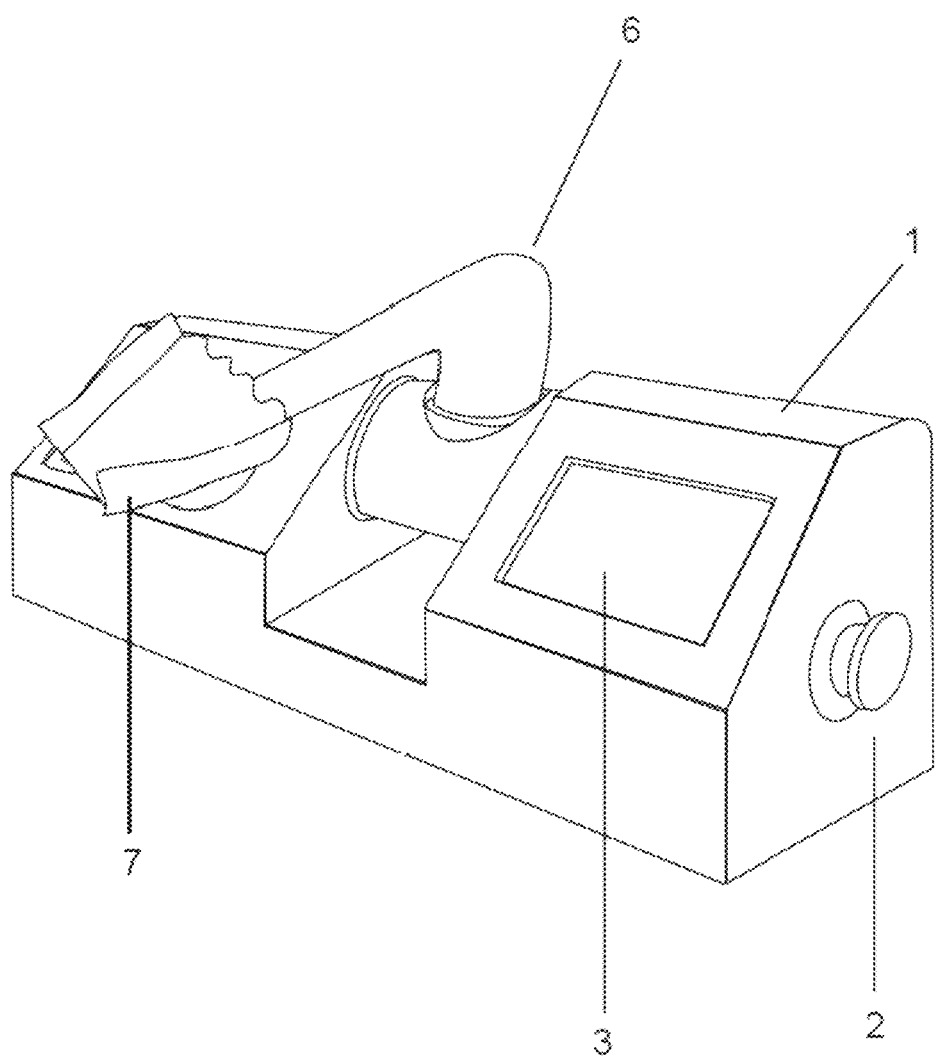
FIG. 2 shows a perspective view of an embodiment of the apparatus having an anatomical-shaped adapter for the end of the upper limb.
Figure 3:
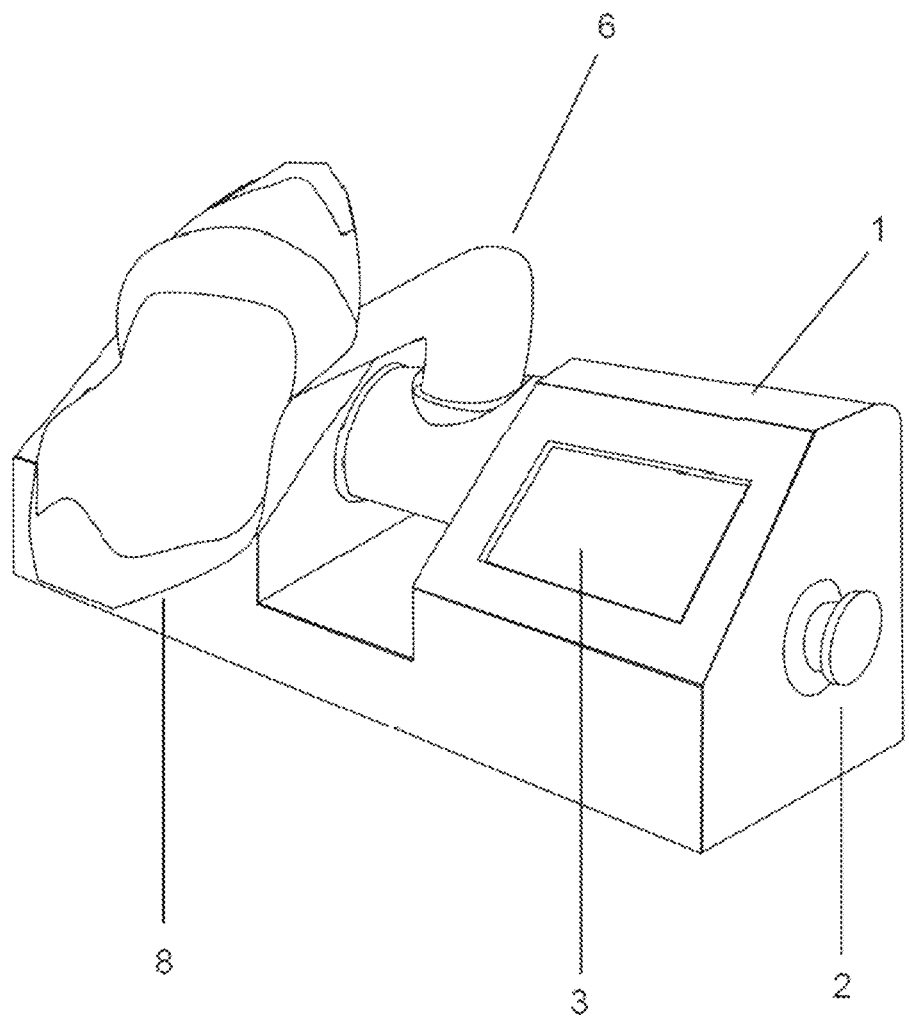
FIG. 3 shows a perspective view of an embodiment of the apparatus having an adapter in pedal form for the end of the lower limb.

Referring initially to FIGS. 1-3, there are illustrated perspective views of embodiments of the motor rehabilitation apparatus for the upper and lower limbs, in which we can observe the apparatus (1), the emergency button (2), the tablet (3), the biometric reader (4), and the robotic arm (6). The embodiments of FIGS. 1-3 include, respectively, a sphere-shaped adapter for the end of the upper limb (5), an anatomical-shaped adapter for the end of the upper limb (7), and adapter in pedal format for the end of the lower limb (8).

The apparatus (1) can be used by patients with neurological, musculoskeletal, muscular, rheumatic, motor and/or cognitive diseases or injuries; patients who suffered accidents or physical traumas; patients who are under a recovery process after surgery; patients who have to correct or re-learn motor movements; patients who have to perform preventive training so as to prevent the progression of disease; and for individuals in search of training and physical fitness.

The apparatus (1) works with movements and exercises in three-dimensional space. It is able to leave the limb suspended in space and under the influence of gravity. It permits movements along a curvilinear trajectory.

With these features, the movements and exercises become more complex and integrated, and are more similar to those that people perform in their daily life activities. These exercises also require greater muscular activation and the use of a greater number of muscular groups and joints of the limb. In this way these exercises promote greater brain stimulus, in which the brain will have to recruit a higher number of neural circuits to execute the exercises, which lead to a more complete, faster and more effective rehabilitation of the individual's capacity.

The apparatus (1) can also be employed successfully in the evaluation, diagnosis and monitoring of the patient's rehabilitation because it allows the measurement of the force, the spatial trajectory, the velocity, the accuracy and other diagnostic and follow-up variables, which make it possible to obtain accurate and objective numerical data for a more careful evaluation and for the establishment of a more effective and faster rehabilitation plan.

In cases of training and physical fitness, the apparatus permits the practice of exercises and movements directed toward a faster and more effective development of the individual, setting the exercises in an entertaining and motivating virtual environment, with colors, sounds and games.

Figure 4:
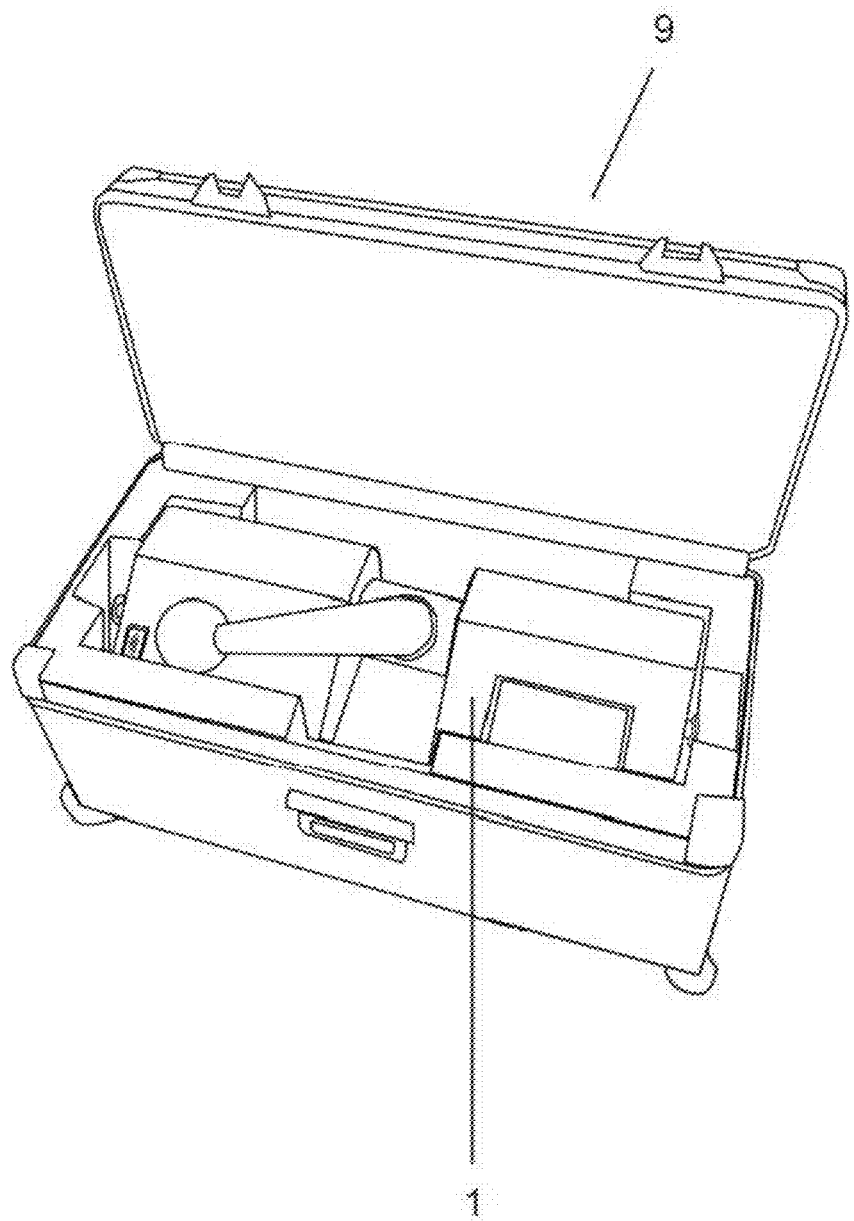
FIG. 4 shows the apparatus inside a carrying case.

The apparatus is compact, lightweight, easy to transport and does not require previously prepared facilities for its installation. FIG. 4 shows the apparatus (1) inside a carrying case (9). It can be transported inside the carrying case (9), which allows its use in the patient's home, in rehabilitation clinics, in physiotherapy clinics, in medical clinics, hospitals and in sport centers.

Figure 11:
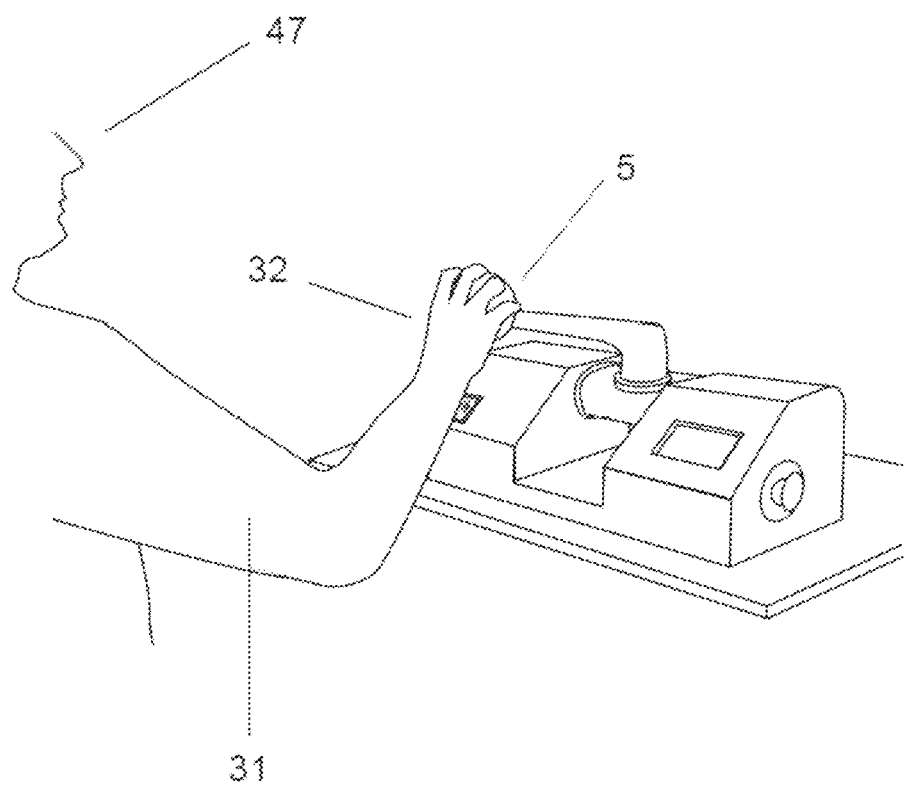
FIG. 11 shows an embodiment of the apparatus in use with an upper limb.
Figure 12:
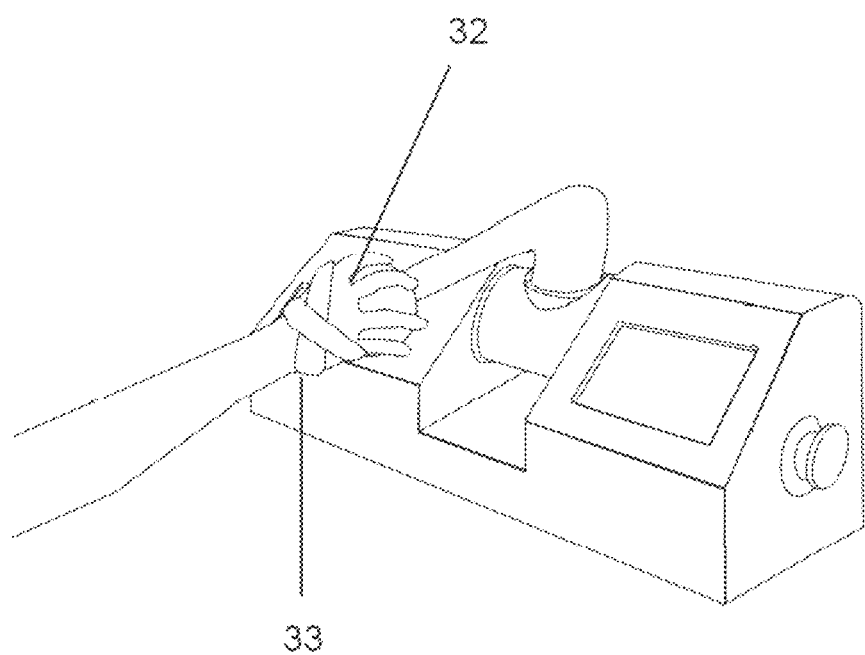
FIG. 12 shows another embodiment of the apparatus in use with the upper limb.
Figure 13:
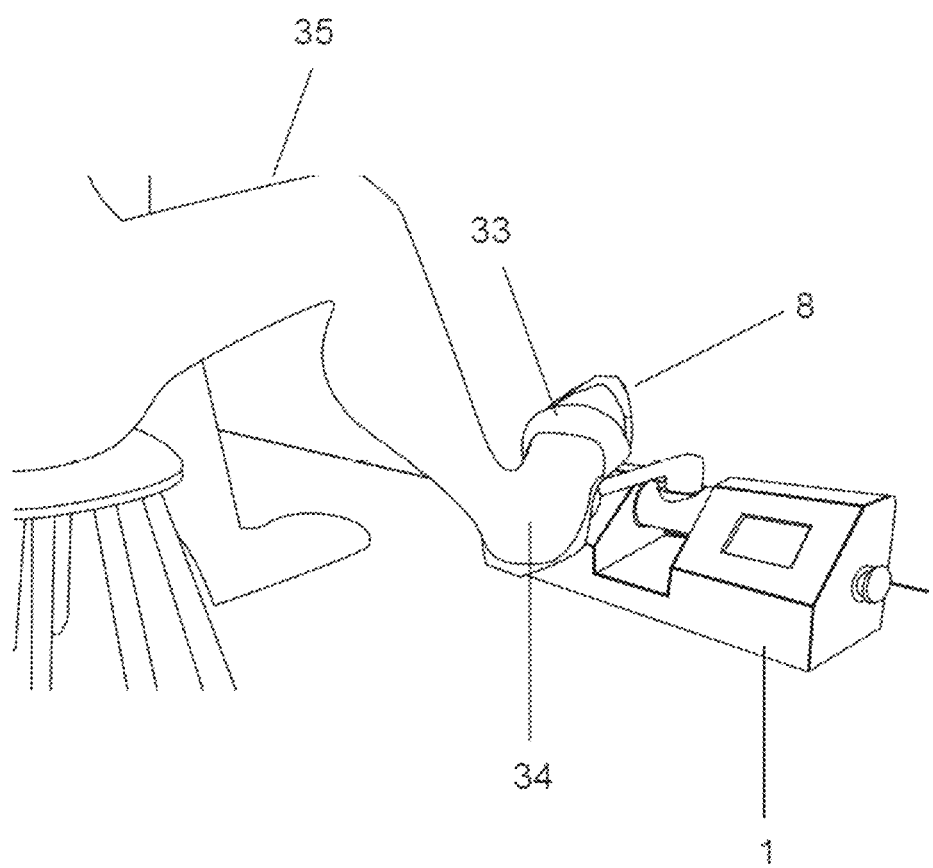
FIG. 13 shows an embodiment of the apparatus in use with a lower limb.

Referring now to FIGS. 11-13, embodiments of the apparatus are shown in use. FIG. 11 shows the patient (47) with the upper limb (31) and the hand (32) on the adapter (5), demonstrating that the patient's limb is suspended in three-dimensional space and connected to the apparatus only by the adapter (5). FIG. 12 shows the patient's hand (32) connected to the adapter through straps having hook and loop fasteners (33). FIG. 13 illustrates the patient's foot (34) connected to the adapter (8) by straps with hook and loop fasteners (33), where it is possible to observe that the leg (35) is suspended in three-dimensional space and that the apparatus (1) is positioned on the floor.

In use, the apparatus should be placed on a table if the exercises are for the upper limbs, or on the floor if the exercises are for the lower limb. The patient should be seated or standing in front of the apparatus. The hand (32) or foot (34) should be connected to the adapter (5, 7 or 8) by a glove or sock, tapes, or straps with hook and loop fasteners (33).

For the upper limb rehabilitation cases, the adapter has preferably the shape of a sphere (5) or an anatomical shape (7) for the patient's fingers or hand, but also it is possible to employ an adapter in the form of a handle, a joystick or another format that allows the patient's hand to grip.

In the lower limb rehabilitation cases, the adapter will have preferably the shape of a sphere, an ellipsoidal, a plate, a pedal (8) or other form that allows positioning of the foot.

In terms of materials, the adapter (5, 7 or 8) will be made preferably of silicon, but plastics, polymers, elastomers, foams, woods, metals or other materials can be employed, and may include superficial coverings, textures, or relieves that may facilitate the connection with the patient's distal end or stimulate tactile aspects or the individual's sensitivity.

It is important to emphasize that the only point of connection of the patient's limb with the apparatus is through the adapter, which leaves the limb (31, 35) suspended in space, without any support or sustaining apparatus, under the action of gravity and free to move in three-dimensional space, which permits rehabilitation exercises and movements to be very similar with the movements that the person performs in daily life activities and leads to faster and more effective results.

Figure 5:
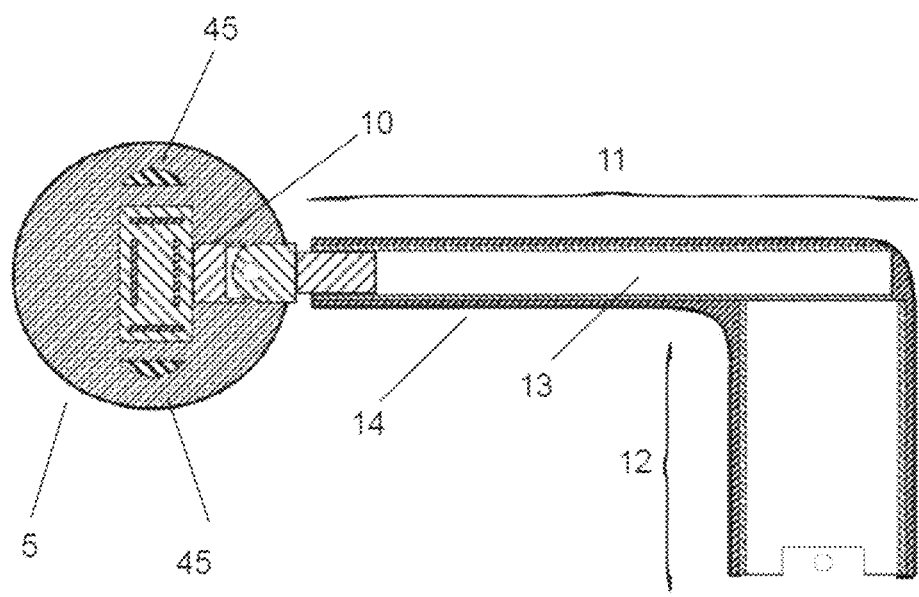
FIG. 5 shows a cut-away view of a robotic arm of the apparatus.

FIG. 5 shows a cut-away view of the robotic arm, showing the sphere-shaped adapter (5), the universal joint (10), the sensor (45), the larger rod (11), and the smaller rod (12). In this figure it is possible to see that the larger rod and the smaller rod have a core (13) and a superficial covering (14).

The adapter (5, 7 or 8) can be fixed on the robotic arm (6) or can contain, inside, a universal joint, a bearing system, or a spherical joint (10) to allow mobility in relation to the robotic arm (6), such that preferably the bearing system, universal joint, or the spherical joint will be used to allow the rotational movement of the adapter in relation to the robotic arm, leading to a larger number of possible movements of the patient's limb.

The adapter can contain sensors (45) internally so that the patient may press it and obtain visual, audible, or other type of effects on the screen of the virtual and/or augmented reality software, which stimulates the cognitive function of the brain together with the exercise for the individual's motor system.

The robotic arm (6), is preferably formed by a larger rod (11), with length varying between about 1 cm and about 100 cm, and a smaller rod (12), with length between about 5 cm and about 50 cm.

The rods can be straight or have some type of curvature and the union between them can form any angle with each other.

It is also possible to have the robotic arm with the smaller rod, whether straight or with some curvature, and with length between about 5 cm and about 100 cm.

The robotic arm (6) can be solid and made of metal, plastic, wood, polymer or other type of material, having or not superficial coverings, relieves, or textures. It can also be manufactured with a core made from these materials and can have a superficial covering, relief, or texture made with the mentioned materials. In a preferential configuration, the robotic arm will have a metal core (13) and a plastic covering (14).

On one end, the robotic arm (6) is connected to the adapter for the patient's hand or foot and, on the other end, it is connected to a gear system, with satellite arrangement, such that its fixation to the gear system is done through screws, pins, adhesives, glue or other fixation element.

Figure 6:
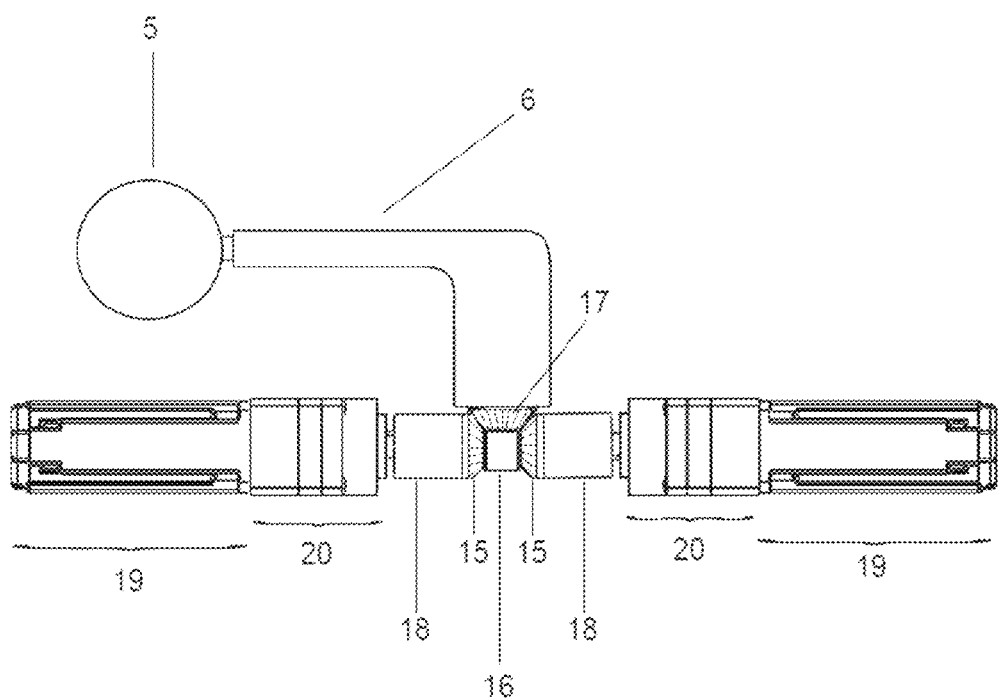
FIG. 6 shows a view of the robotic arm and drive system.

FIG. 6 shows a view of the robotic arm (6), the sphere-shaped adapter (5), the gear system composed of opposing gears (15), the connection element (16) and the spider gear (17), the bushings (18) which interconnect each opposing gear to a motor (19) and the gear reduction boxes (20).

Figure 7:
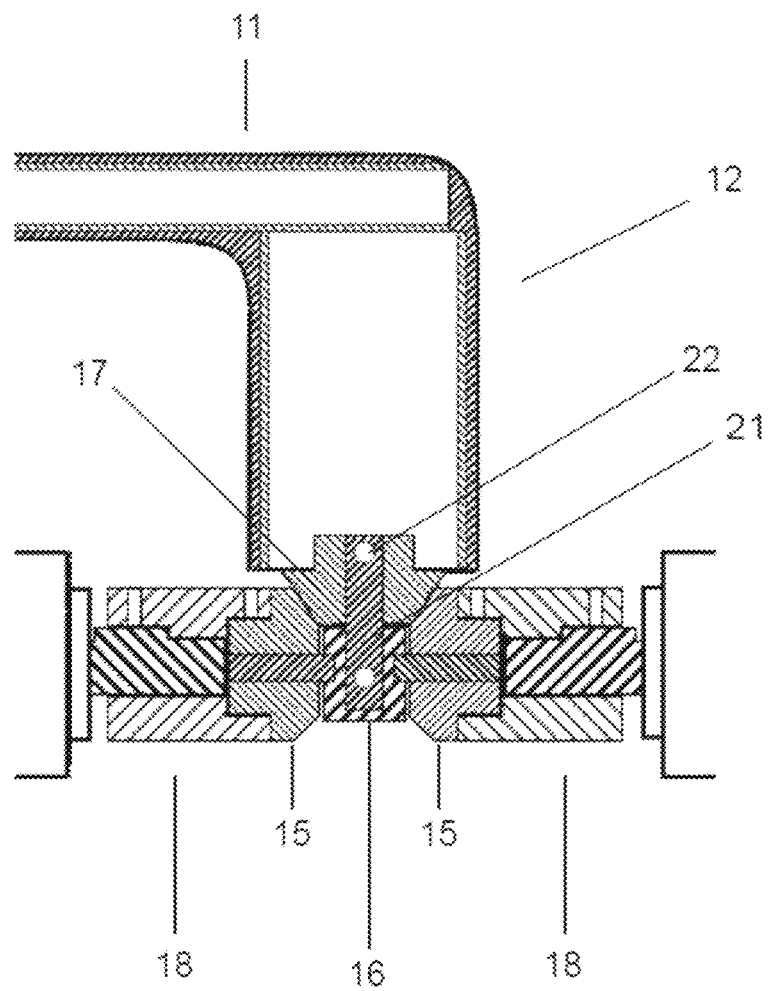
FIG. 7 is a cross-sectional view of the gear system.

FIG. 7 is a cross-sectional view of the gear system that shows the opposing gears (15), the connection element (16), the spider gear (17), the fixation pin (21) from the spider gear to the connection element, the fixation screw (22) of the spider gear in the smaller rod (12) of the robotic arm, the larger rod (11) and the bushings (18).

The gear system is composed of two opposing gears (15), a spider gear (17), and a connection element (16) that is positioned between them.

The gears are conic or semi-spherical, may have straight or helical teeth and may have or not a mechanism to prevent clearances or backlash.

The connection element (16) between the gears may have the shape of polygonal or circular base prism, shape of a sphere, or shape of a polyhedron. It is connected to the spider gear (17) through a fixation pin (21) and is in contact with the opposing gears (15), maintaining the connection between the three gears.

The spider gear (17) is connected to the robotic arm (6) and is in a position perpendicular to the opposing gears (15).

Each opposing gear is connected to a motor (19) through a semi-axle and/or a bushing (18) and there can be or not a gear reduction box (20) between the opposing gear (15) and the corresponding motor (19).

Figure 8:
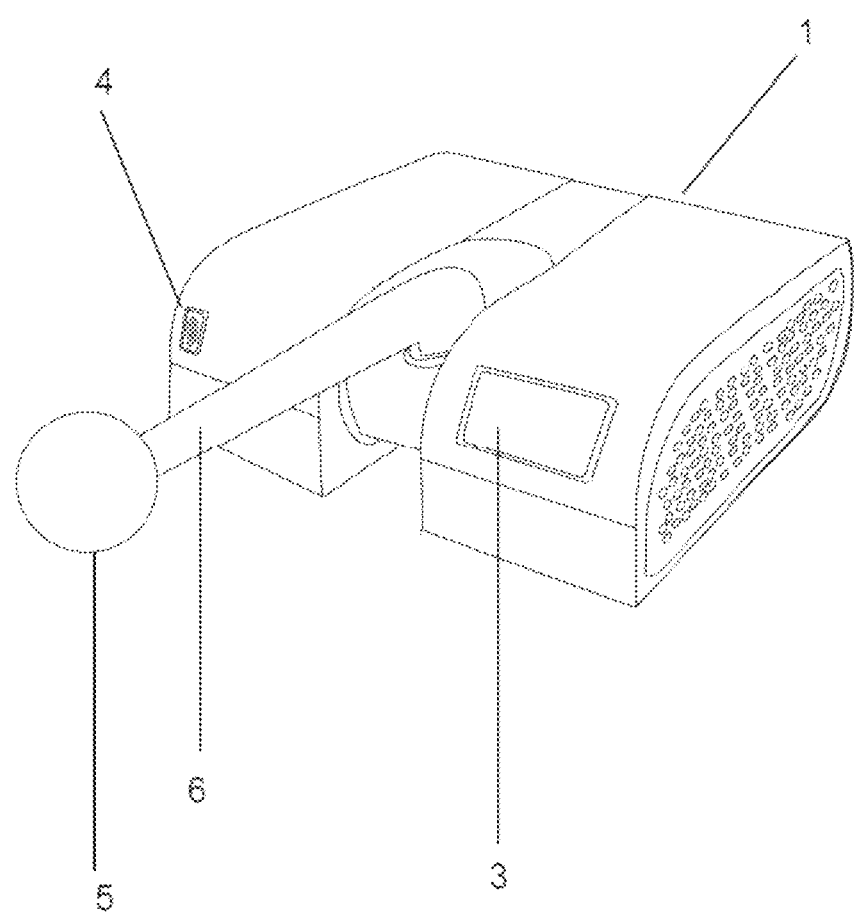
FIG. 8 shows a perspective view of the apparatus in its external configuration.

FIG. 8 shows the apparatus (1) in its external configuration with the motors positioned perpendicularly to the axis of the opposing gears, which also presents the sphere-shaped adapter (5), the robotic arm (6), the tablet (3) and the biometric reader (4).

The combination of movements of the gears generates a wide range of trajectories for the robotic arm and for the patient's limb in three-dimensional space, making possible the execution of several rehabilitation and training and physical fitness movements and exercises.

Without being exhaustive, but for the purpose of illustrating some combinations of these movement of the gears and their results in the trajectories of the robotic arm and the patient's limb, the inventors present the following examples, with reference to FIGS. 14-19.

Figure 14:
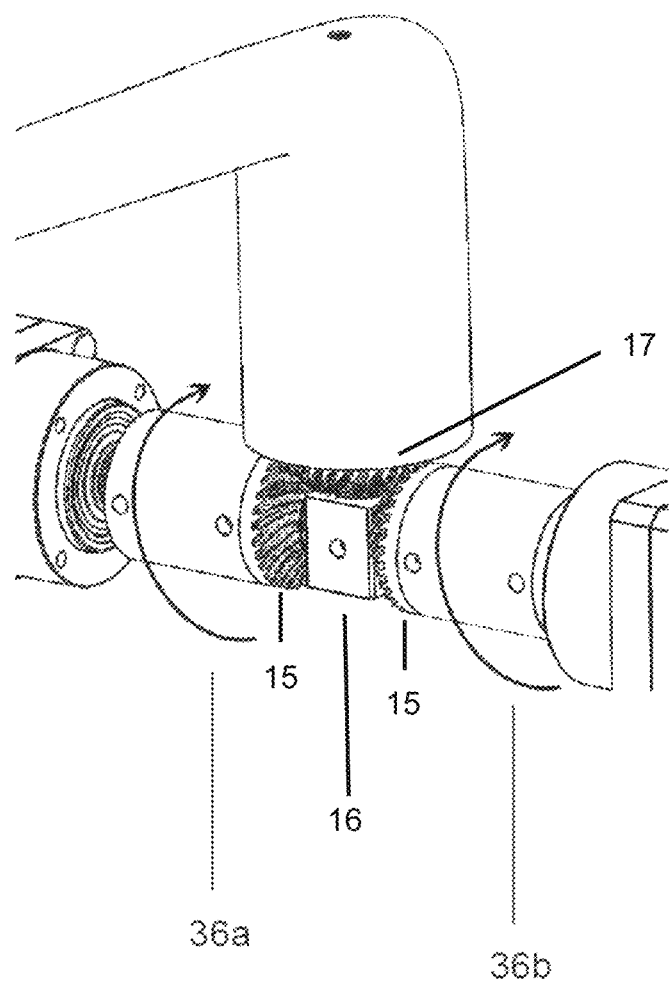
FIG. 14 shows an exemplary motion of opposing gears of the apparatus.
Figure 15:
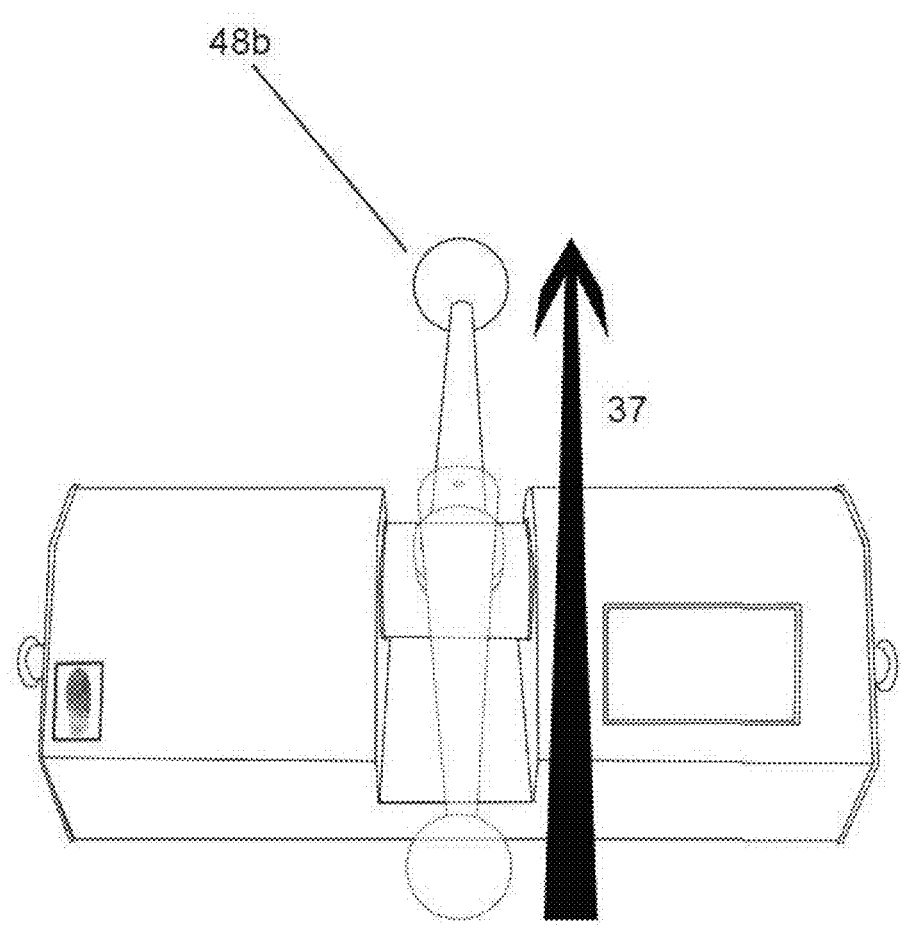
FIG. 15 shows the trajectory of the robotic arm corresponding to the gear motion of FIG. 14.

FIG. 14 shows the opposing gears (15) with rotations (36a and 36b) in the same direction around a common axis. When the two opposing gears (15) have rotations in the same direction around a common axis and with the same magnitude (36a and 36b), the connection element (16) and the spider gear (17) trace a curvilinear trajectory on a plane perpendicular to the horizontal axis of the opposing gears, causing the robotic arm and the patient's limb to describe the curvilinear trajectory (37) on this same perpendicular plane, leading the robotic arm from the position (48a) to the position (48b), as shown in FIG. 15 wherein initial position (48a) of the robotic arm is shown in a lighter color tone and the final position (48b) in a darker tone.

Figure 16:
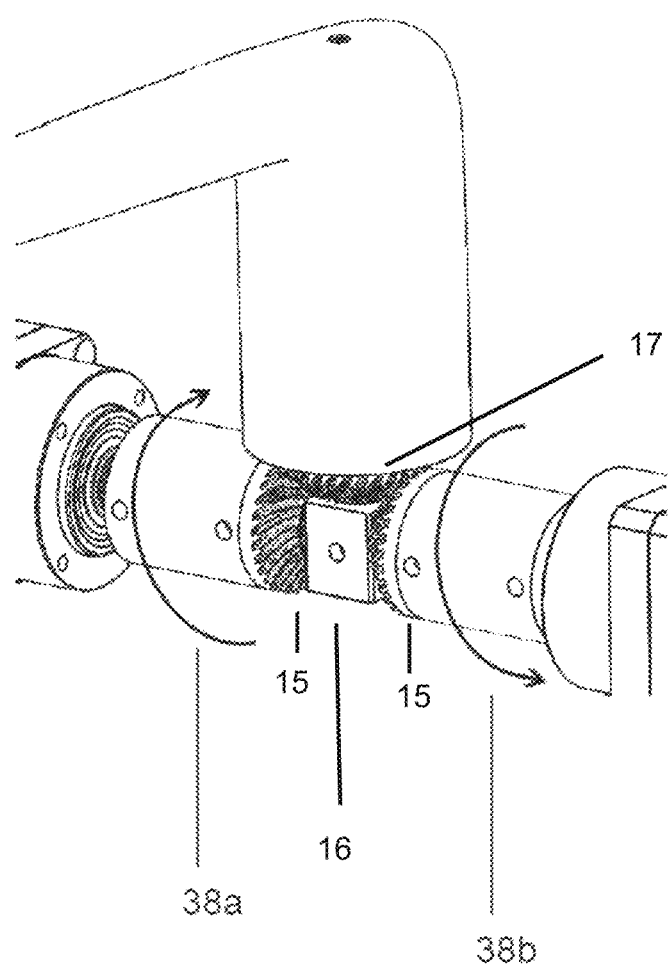
FIG. 16 shows another exemplary motion of the opposing gears.
Figure 17:
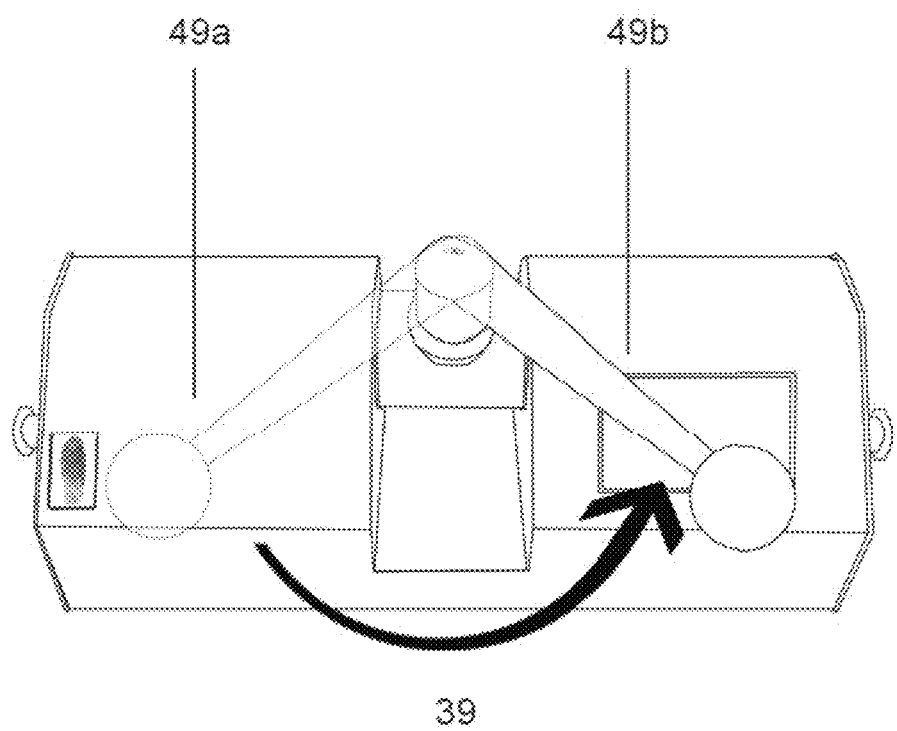
FIG. 17 shows the trajectory of the robotic arm corresponding to the gear motion of FIG. 16.

FIG. 16 shows the opposing gears (15) with rotations (38a and 38b) in opposite directions around a common axis but with the same magnitude. In this situation, the spider gear (17) rotates around its own central axis, the connection element (16) remains in the same place, and the robotic arm and the patient's limb trace a movement (39) with curvilinear trajectory on a plane perpendicular to the central axis of the spider gear, as shown in FIG. 17. With these rotations, the robotic arm is moved from the initial position (49a) to the final position (49b), where FIG. 17 shows the initial position (49a) of the robotic arm in a lighter color tone and the final position (49b) in a darker tone.

Figure 18:
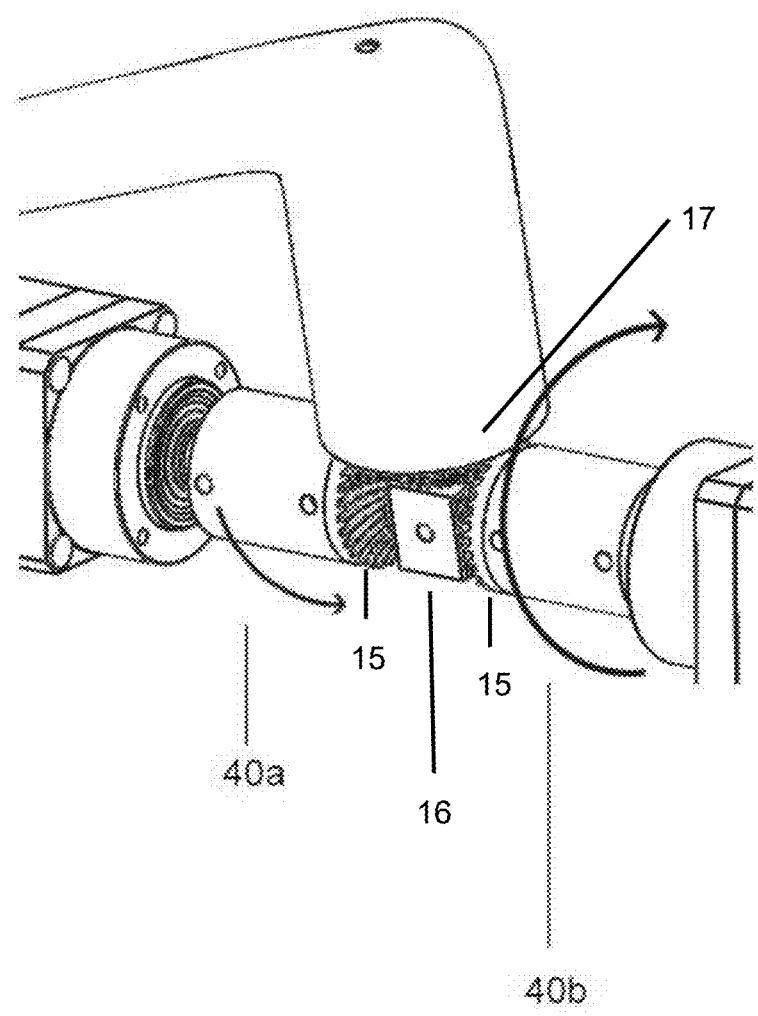
FIG. 18 shows another exemplary motion of the opposing gears.

FIG. 18 shows the opposing gears (15) with rotations with different magnitude (40a and 40b) and in opposite directions. In this case, the connection element (16) and the spider gear (17) move on planes oblique to the horizontal plane which intersects the axis of the opposing gears, causing the robotic arm and the patient's limb to move in curvilinear oblique trajectories in three-dimensional space.

Figure 19:
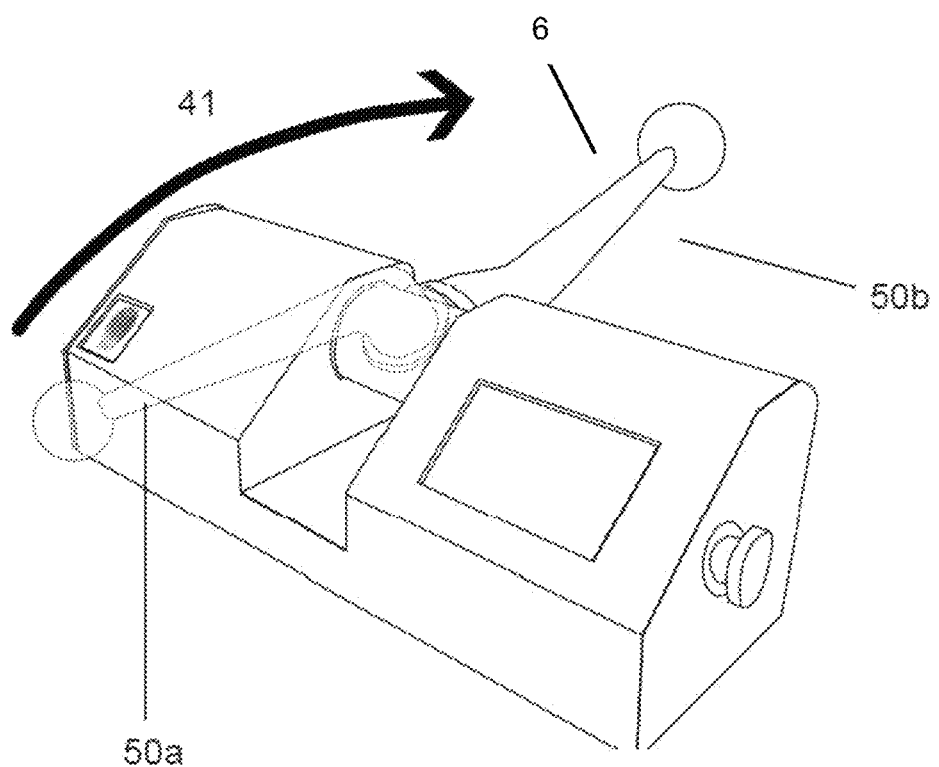
FIG. 19 shows the trajectory of the robotic arm corresponding to the gear motion of FIG. 18.

FIG. 19 shows the trajectory (41) of the movement of the robotic arm (6), which is generated by the rotations (40a and 40b) shown in FIG. 18. With these rotations, the robotic arm (6) traces, in three-dimensional space, a movement with curvilinear trajectory and oblique to the horizontal plane that cuts the axis of the opposing gears. FIG. 19 shows the initial position (50a) of the robotic arm in a lighter color tone and the final position (50b) in a darker tone, with the apparatus shown in perspective view.

The motors (19) have torque between about 0.05 Nm and about 50 Nm and have position sensors that will transmit information to the management and control system.

Motors (19) can be aligned with the corresponding opposing gears (see FIG. 6) or can be positioned perpendicularly to them, such that, in this case, the transmission of the movement from the motor to the opposing gear will use a connector or an "L"-shaped gear reduction box.

Figure 9:
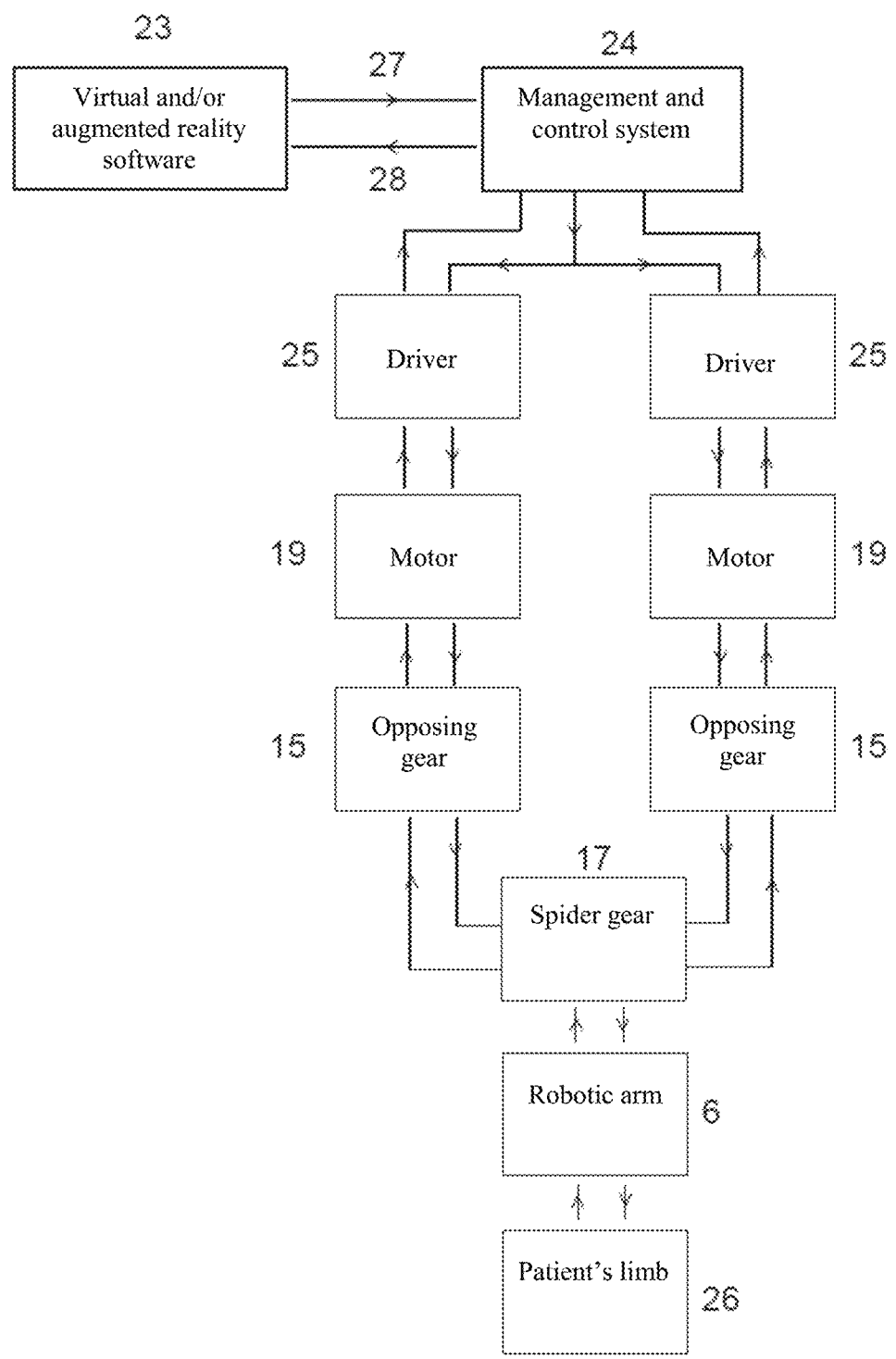
FIG. 9 is a schematic drawing of the functional relation between the apparatus, a control system, and software.

Referring now to FIG. 9, a schematic drawing is shown of the relation between the virtual and/or augmented reality software (23), the management and control system (24), the drivers (25), the motors (19), the opposing gears (15), the spider gear (17), the robotic arm (6) and the patient's limb (26). In the figure the forward information path (27) and its feedback path also appear (28).

Preferably each motor (19) is connected to a driver (25), which is a converter of logical signals into electrical signals, and there is a connection between the two drivers of the apparatus for data synchronization. However, it is possible that there be only one driver, serving the two motors.

The driver receives the logical signals coming from the management and control system (24), and converts these logical signals into electrical signals which will be sent to the motors (19) to generate the rotations and torques in the gears.

The management and control system (24) receives information (27) from the virtual and/or augmented reality software (23) and manages and controls in real time the data transmissions between the virtual and/or augmented reality software (23), the drivers (25), the motors (19), thus controlling the movement of the gears (15 and 17), the robotic arm (6) and the patient's limb.

Internally, the virtual and/or augmented reality software (23) keeps the information and data of the movements that will be applied in the motor rehabilitation exercises or in the training and physical fitness exercises, by transmitting this information (27) to the management and control system (24), which calculates the trajectory to be performed by the patient, and also the force and acceleration of the movement, and send logical signals to the drivers (25), which will convert them into electrical signals that will produce the movement of the motors (19), generating rotations and torques in the gears.

With this, we will have the movements of the gears, the robotic arm and the patient's limb in a given trajectory, with certain force and certain acceleration.

The management and control system (24) also receives feedback (28) with the information on the patient's movements, compares with the information received from the virtual and/or augmented reality software, recalculates trajectories and sends signals to the motors to carry out rotations and torques to correct the trajectory, the force and the acceleration of the patient's movement.

Figure 10:
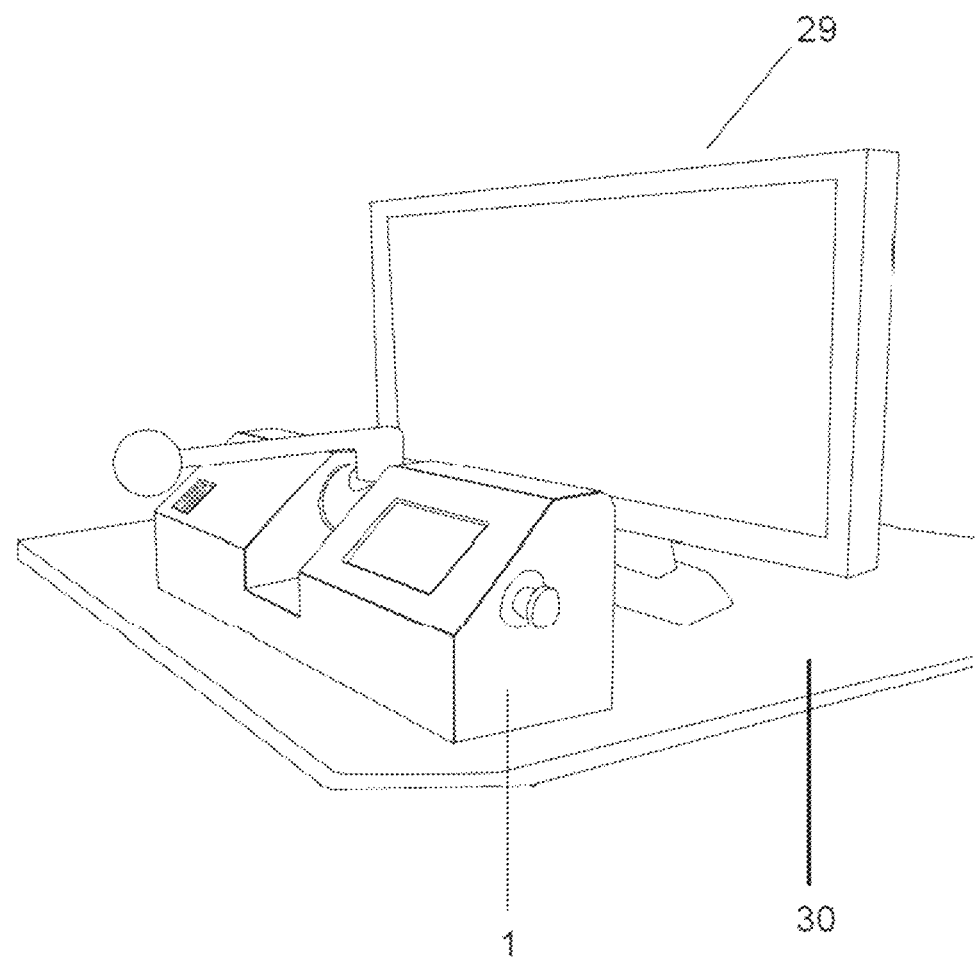
FIG. 10 shows the apparatus with cooperating hardware for a virtual environment.

FIG. 10 shows the apparatus (1) with a monitor (29) which shows the games, scenarios and virtual environments of the virtual and/or augmented reality software (23). The apparatus and monitor are both are positioned on a table (30).

In the visual interaction with the patient, the virtual and/or augmented reality software (23) shows, on a computer monitor (29), on a television screen, on a projector or on any other visual media, games, scenarios and environments with figures, colors and sounds to simulate people's daily life situations, presenting to the patient a friendly, entertaining and motivating graphical interface.

To facilitate the patient's immersion into the games and in the virtual scenarios and to expand the cognitive stimuli, virtual and/or augmented reality glasses can be employed. However, the virtual and/or augmented reality software operates normally without the use of glasses.

For the purpose of illustrating the interaction among the various components of the motor rehabilitation apparatus for the upper and lower limbs, some additional examples will be presented in the following paragraphs, which should not be considered exhaustive or limiting of any aspect of this invention.

Figure 20:
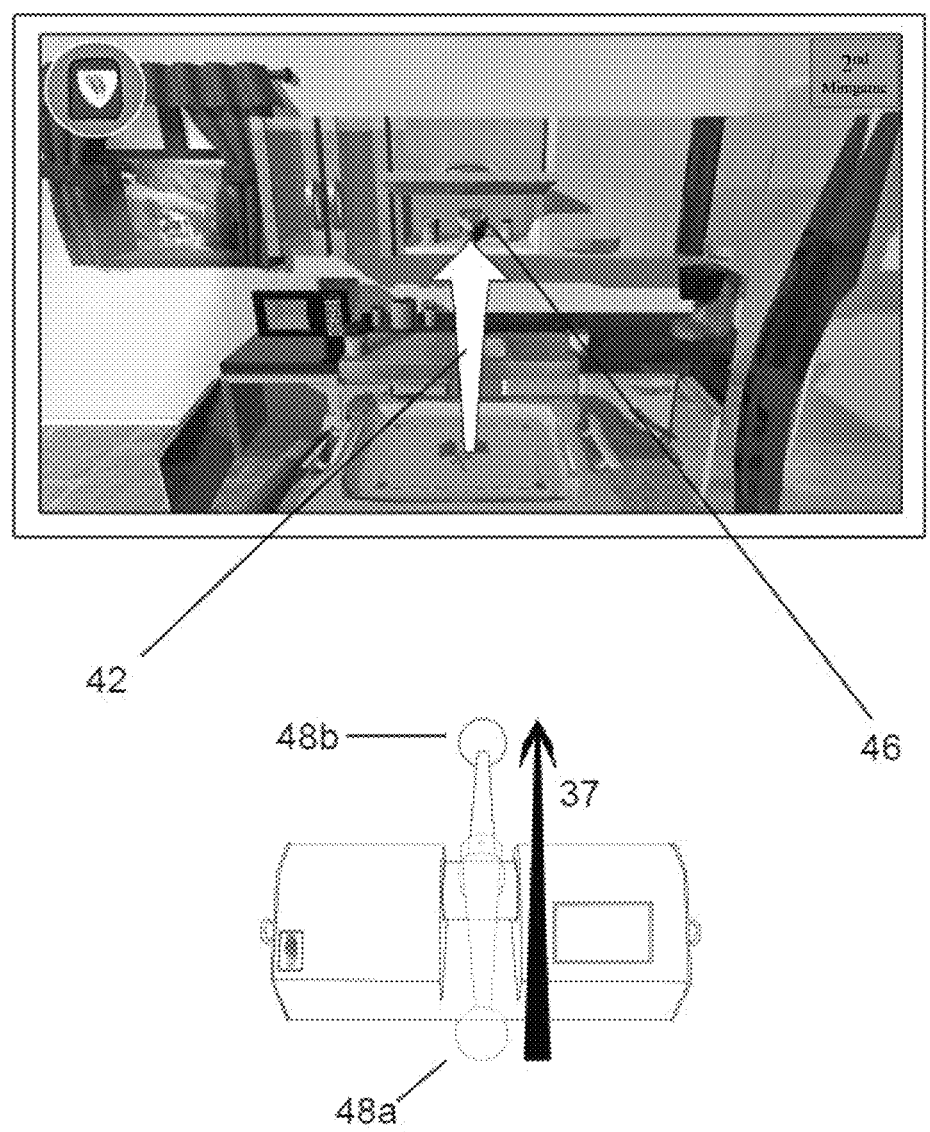
FIGS. 20-22 show exemplary trajectories of robotic arm movements, with correspondence shown by the virtual and/or augmented reality software.

Referring to FIG. 20, consider a rehabilitation movement (42) of the upper limb, which consists in picking up an object on a table and placing it in a cupboard in front of the table by means of a curvilinear trajectory in three-dimensional space. The virtual and/or augmented reality software transmits the information and data from the movement (42) to the management and control system, which calculates the trajectory, force and acceleration necessary to execute this movement. This information or logical signals are transmitted to the drivers, where they are converted into electrical signals, which are transmitted to the motors, which in turn, transmit rotations and torques to the opposing gears that move the connection element and the spider gear, producing the movement (37) of the robotic arm, which moves the patient's limb. The movement transmitted to the patient's limb will be shown on the screen and the patient will view his/her virtual hand (46), which will allow a stimulus not only of the cognitive function but also of the motor system of the patient.

FIG. 20 shows the initial position (48*a*) of the robotic arm in a lighter color tone and the final position (48*b*) in a darker tone. The virtual and/or augmented reality software may typically use colors to provide the entertaining aspects of the scenario and the motivating environment that is similar to the patient's daily life.

The virtual trajectory (42) of the movement has a straight trajectory (37) in three-dimensional spherical space. This is possible because the opposing gears have rotation in the same direction around a common axis and the same magnitude (36*a* and 36*b*), see FIG. 14. With this, the connection element, the spider gear, the robotic arm and the patient's limb trace a curvilinear trajectory (37) on a plane perpendicular to the horizontal axis of the opposing gears.

In case the patient exerts any force opposite to the planned movement or deviates from the trajectory assigned for the exercise, the management and control system receives this feedback, recalculates the trajectory, the force and/or acceleration, sends these data in form of logical signals to the drivers, which will send electrical signals to the motors to transmit rotations and torques to the gears, with the objective of correcting the trajectory, the force and/or the acceleration of the patient's movement. At the same time, the management and control system will send logical signals to the virtual and/or augmented reality software showing the corrections of the trajectory of the upper or lower limb on the screen or on the monitor.

Figure 21:
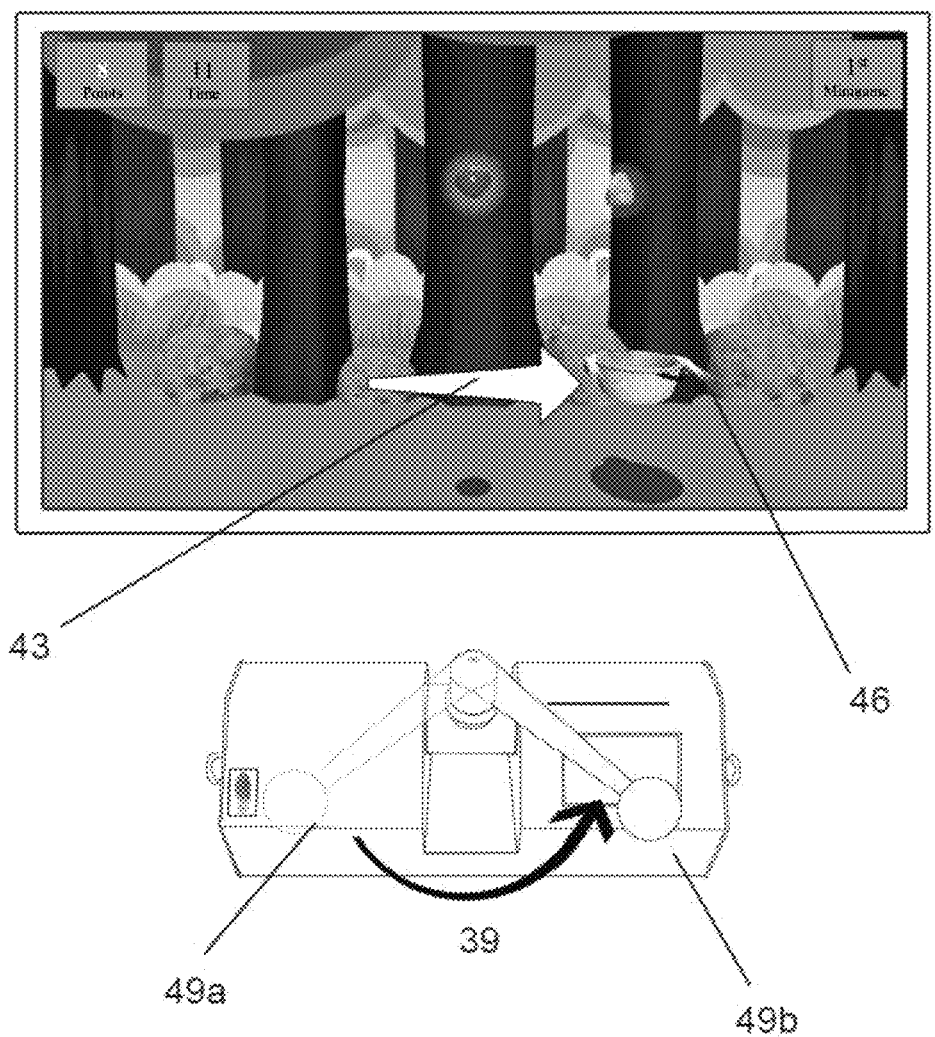

Referring to FIG. 21, if the desired movement (43) for the patient's exercise was to move an object laterally on a horizontal plane in a given environment, the information transmission sequence would be the same as described above; however, the movement of the opposing gears would have rotations in opposite directions around a common axis and the with same magnitude. With this, the spider gear would rotate around its own central axis, the connection element would remain in the same position and the robotic arm and the patient's limb would make a lateral movement with curvilinear trajectory on a horizontal plane parallel to the horizontal axis of the opposing gears. With this, the patient would see on the screen of the virtual and/or augmented reality software the movement (43) and the virtual hand (46) and the apparatus would describe the curvilinear trajectory (39) which leads the robotic arm from the position (49*a*), shown in a lighter color tone, to (49*b*), shown in a darker color tone.

Figure 22:
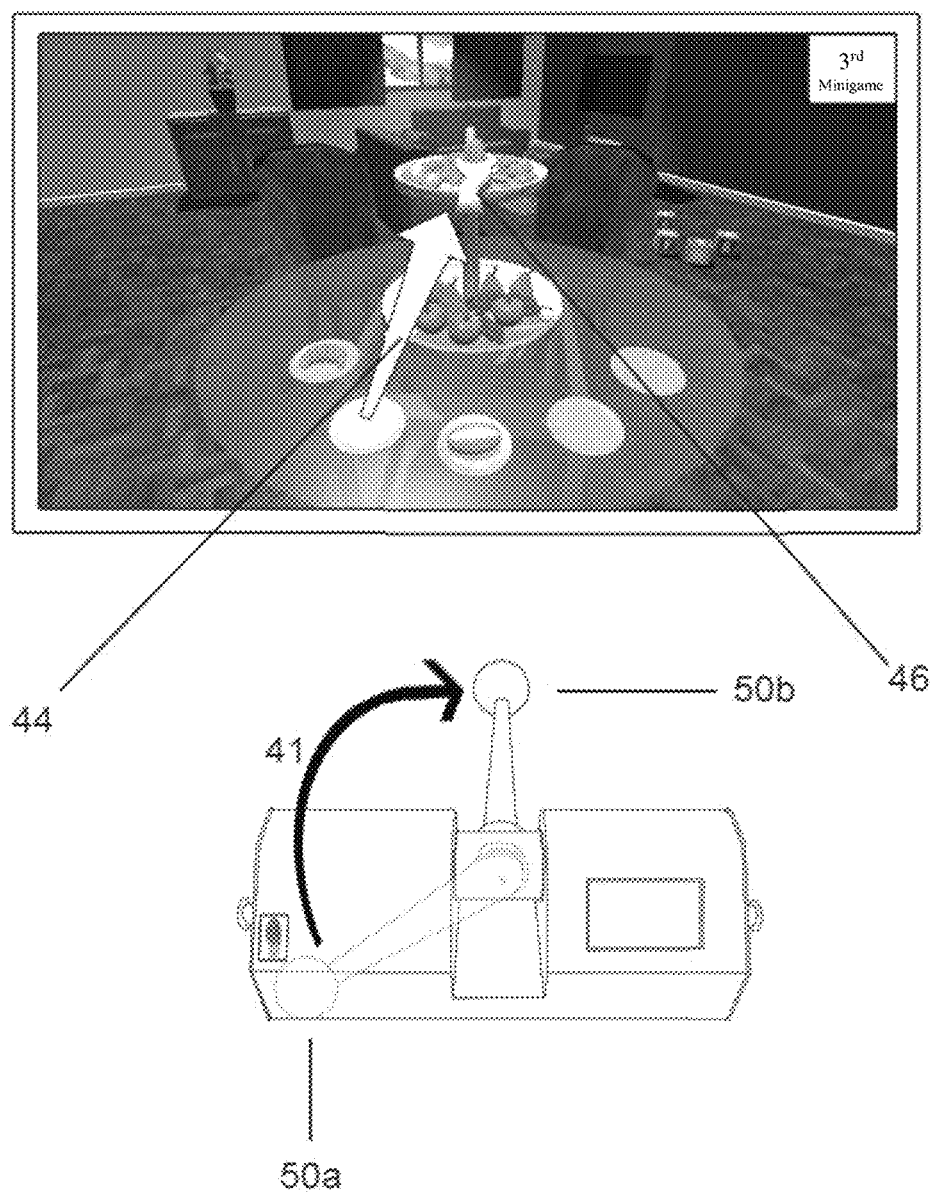

In another situation, as can be seen in FIG. 22, if the exercise was to pick up a fruit on a plate on the table and to place it in a fruit basket located in a place above and to the right of the fruit's initial position, the virtual and/or augmented reality software would send the information from the movement to the management and control system, which would calculate its trajectory, force and acceleration, sending these data to the drivers, which would transmit this information to the motors that would generate rotations and torques. With this, the opposing gears would rotate in opposite directions in relation to a common axis and with different magnitude, causing the connection element, the spider gear, the robotic arm and the patient's limb to describe a movement (41) in three-dimensional space in a curvilinear oblique trajectory in relation to the horizontal plane which intersects the horizontal axis of the opposing gears. The patient would view the movement (44) on the screen, together with the virtual hand (46), and the end of the robotic arm would describe the trajectory (41), going from position (50*a*) to (50*b*). FIG. 22 shows the initial position (50*a*) of the robotic arm in a lighter color tone and the final position (50*b*) in a darker tone, with the apparatus shown in a frontal view, carrying the same movement presented in FIG. 19 in the perspective view.

Aside from its application in rehabilitation exercises, the apparatus can also be used for training and physical fitness exercises. In this case, the apparatus works predominantly in the active-assistive mode, offering resistance to the movement to be performed by the person, so that the effort may be more intense and guided, providing a faster and more efficient physical fitness exercise.

During the development of the apparatus presented herein, the inventors performed several clinical trials and obtained excellent results, increasing the efficacy of the rehabilitation exercises, improving the patients' responses and engaging the patients in the treatment.

In one of the clinical trials, the force, the trajectory, the velocity and the accuracy of the movements of 8 patients with injuries and sequelae resulting from stroke were assessed to establish the initial situation of each case and to define the rehabilitation treatment to be applied. These patients are considered chronic by the conventional motor scales.

Next, 18 rehabilitation sessions were carried out with a duration of 1 hour each, such that each patient executed between 690 and 900 reaching movements per session with the injured limb. These movements generated flexion, extension, abduction and adduction of the shoulder; extension and flexion of the elbow; flexion, extension, adduction and abduction of the wrist; ipsilateral movements; and contralateral movements.

After 18 rehabilitation sessions, an assessment of the patients was carried out once more and an improvement in the motor and functional performance of the patients' limb was confirmed, with larger amplitude of movement of the shoulders, elbow, and wrist; improvement in flexion, extension, internal and external rotation, abduction and adduction of the limb; greater accuracy of the trajectory in the movements; and improvements of the force and the velocity of the movements.

It is worth emphasizing that if these exercises were performed by a physiotherapist, without using the present apparatus, the patient would have performed only 80 to 100 movements per session, which would lead to longer recovery times and less effective recovery.

Another clinical trial was done on chronic patients who presented brain injuries that made performing vertical movements against the force of gravity difficult.

The apparatus was used to assess the initial and final conditions of the patients and it was also employed to exercise these patients.

To perform the exercises, the virtual and/or augmented reality software presented the scenario of picking up an ingredient on the table and placing it in a cupboard, repeating the exercise for 4 other ingredients. Thus, each patient had to perform movements in 5 different trajectories in three-dimensional space.

Before the exercises with the present apparatus, the patients were not able to carry out the vertical movement of placing the ingredient in the cupboard and, after 18 rehabilitation sessions using the apparatus, these chronic patients were able to pick up the ingredient on the table and place it in the cupboard.

Figure 23:
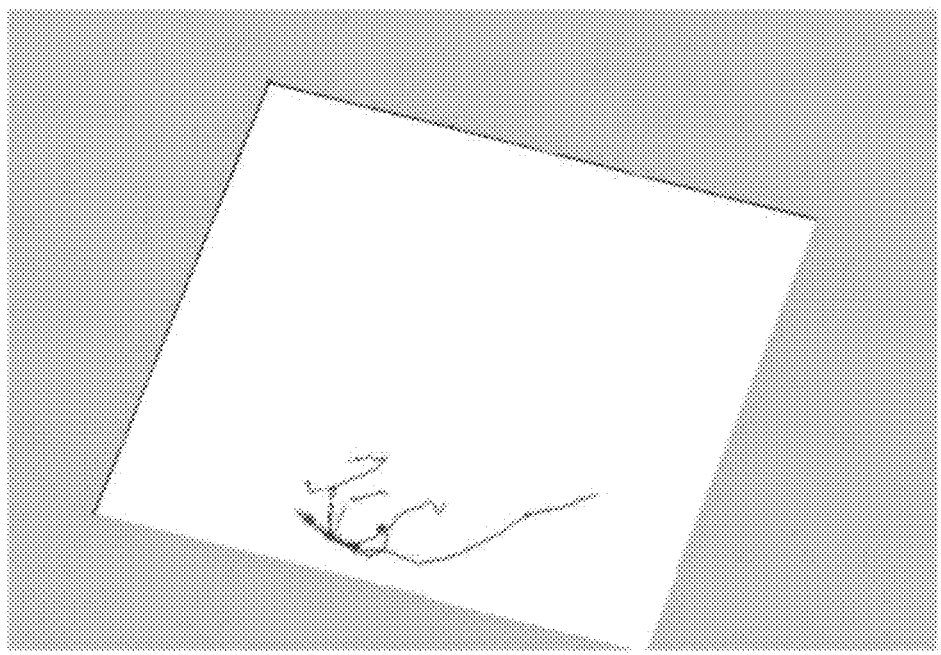
FIG. 23 shows results of a clinical trial before motor rehabilitation treatment.
Figure 24:
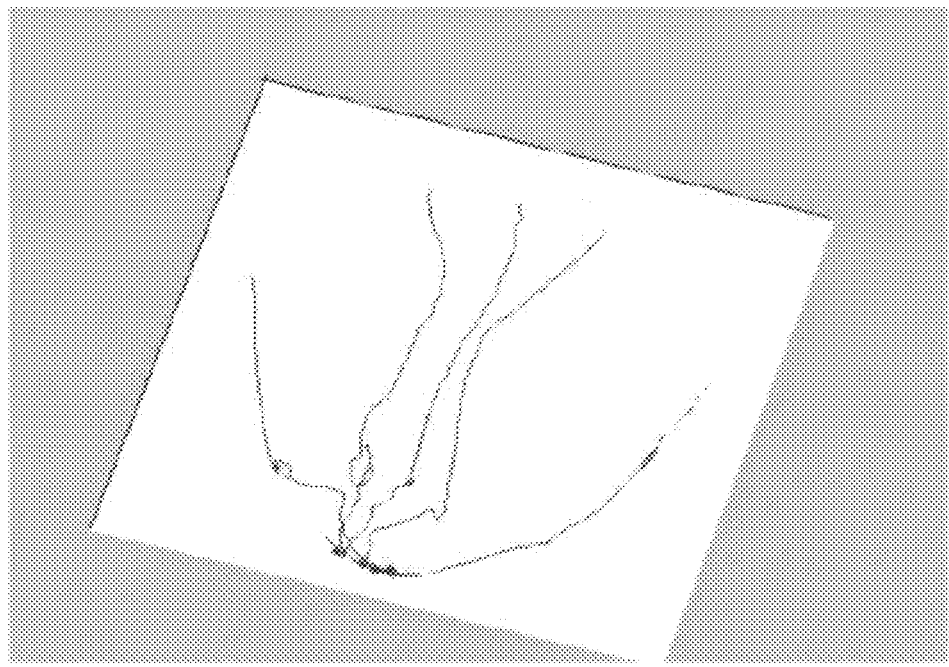
FIG. 24 shows results of the clinical trial after motor rehabilitation treatment with the apparatus.

To facilitate the visualization of this typical example of a patient, FIG. 23 shows the projection, on the two-dimensional plane, of the three-dimensional reaching movement in each of the 5 trajectories before the use of the invented apparatus. FIG. 24 shows the same projection of this reaching movement in 5 trajectories after the rehabilitation treatment with the apparatus.

Observing FIGS. 23 & 24, it is possible to verify that the patient was able to perform the movements with greater amplitude and extension after the treatment with this motor rehabilitation apparatus.

The present apparatus is able to solve the problems of the current state of the technology and to contribute to the expansion of this field of human knowledge, presenting a new and original way of performing therapeutic exercises and movements for motor rehabilitation of the upper and lower limbs and for people's training and physical fitness exercises.

The execution of movements and exercises in three-dimensional space, with the limb suspended, under the action of gravitational force and with curvilinear trajectory represents a great advantage because the movements become more complex and integrated. They are more similar to those that are performed by a person in his/her daily life activities; they require a greater muscular activation; and they move a greater number of muscular groups and limb joints and they produce much more stimulus in the patient's brain leading to a faster and more effective rehabilitation of the individual's capacity.

Another advantage of the apparatus is related to the use of a virtual and/or augmented reality software which has a friendly, entertaining, and motivating graphical interface, which has games, scenarios and environments with figures, colors and sounds, in which the exercises are contextualized in games, scenarios and virtual environments which are very similar to the people's daily life situations. With this, the patient becomes more motivated to execute the exercises because he/she is able to understand the usefulness of the movement, he/she becomes more engaged with his/her own rehabilitation or training, and there is a stimulus not only of the patient motor system but also of his/her cognitive function.

Another advantage of this apparatus is that it is compact, portable, lightweight, easy to transport, and does not require special facilities for its installation and its use because the patient can carry the apparatus home and perform the rehabilitation exercises as many times as he/she can or wishes, which increases his/her speed of recovery. If a person is using the apparatus for training and physical fitness exercises, this advantage continues to be worthwhile because he/she can carry the apparatus to any place and to perform the exercises many times a day.

The possibility of programming the exercises for each patient constitutes another advantage of the invented apparatus because the patient interacts with the apparatus and performs the prescribed exercises for his/her rehabilitation.

Thus, the physiotherapist supervises the exercises and he/she is free to attend to other patients in the same period of time.

The configuration of the gear system is another advantage because it is simple, compact and functional, and allows the execution of movements and exercises in three-dimensional space with the use of only two motors, which contributes to the apparatus being compact, lightweight, easy to transport, and having lower manufacturing cost.

Thus, the present apparatus assists the patients to perform their rehabilitation exercises and helps people to obtain a better and faster physical fitness.

The embodiments of the apparatus and method of use described herein are exemplary and numerous modifications, combinations, variations, and rearrangements can be readily envisioned to achieve an equivalent result, all of which are intended to be embraced within the scope of the appended claims. Further, nothing in the above-provided discussions of the apparatus and method should be construed as limiting the invention to a particular embodiment or combination of embodiments. The scope of the invention is defined by the appended claims.

The invention claimed is:

1. An apparatus for motor rehabilitation of upper and lower limbs, the apparatus comprising:
   a robotic arm having a proximal robotic arm end and terminating in a distal robotic arm end, the robotic arm including a larger rod, having a length between about 1 cm and about 100 cm, and a smaller rod, having a length between about 5 cm and about 50 cm;
   an adapter connected to the distal robotic arm end, and configured for connection to a distal end of the upper or lower limb;
   a gear system operatively coupled to the proximal robotic arm end, the gear system including two opposing gears, a spider gear, and a connection element;
   two motors operatively coupled to the gear system, each of the two motors configured to directly drive one of the two opposing gears and both of the two opposing gears configured to drive the spider gear;
   at least one driver in electrical communication with the motors;
   virtual or augmented reality software;
   a management and control system in communication with the at least one driver and the virtual or augmented reality software;
   a display in communication with the virtual or augmented reality software;
   wherein, the apparatus is configured to move the robotic arm in three-dimensional space with curvilinear trajectories; and,
   wherein, when only the distal end of the upper or lower limb is connected to the apparatus, the limb is suspended in space.

2. The apparatus of claim 1, wherein the adapter has one of: a spherical shape, an anatomical shape corresponding to a finger or a hand, a handle shape, a joystick shape, or a shape configured to be gripped by a hand.

3. The apparatus of claim 2, wherein the adapter has one of: a spherical shape or an anatomical shape corresponding to a finger or a hand.

4. The apparatus of claim 1, wherein the adapter includes sensors configured for actuation by a patient to obtain an effect in the virtual or augmented reality software.

5. The apparatus of claim 1, wherein the adapter has the shape of: a sphere, an ellipsoid, a plate, a pedal, or a shape configured for connection to a foot.

6. The apparatus of claim 1, wherein the connection of the distal end of the upper or lower limb to the adapter includes one of: a glove, a sock, adhesive tape, or a strap having a hook and loop fastener.

7. The apparatus of claim 1, wherein the adapter is formed of silicon, plastics, polymers, elastomers, foams, woods, or metals.

8. The apparatus of claim 7, wherein the adapter includes superficial coverings, textures, or relieves.

9. The apparatus of claim 1, wherein the adapter is connected to the robotic arm by one of: a bearing system, a universal joint, or a spherical joint.

10. The apparatus of claim 1, wherein the larger rod and the smaller rod are substantially straight and are joined at an angle relative to one another.

11. The apparatus of claim 1, wherein the larger rod and the smaller rod each have a curvature.

12. The apparatus of claim 1, wherein the robotic arm is formed of silicon, plastics, polymers, elastomers, foams, woods, or metals.

13. The apparatus of claim 12, wherein the robotic arm has a core and a superficial covering, relief, or texture.

14. The apparatus of claim 13, wherein the core of the robotic arm is formed of metal and the superficial covering is formed of plastic.

15. The apparatus of claim 1, wherein the robotic arm is affixed to the spider gear.

16. The apparatus of claim 1, wherein each of the two opposing gears is connected to one of the two motors through a semi-axle or a bushing.

17. The apparatus of claim 1, wherein a fixation pin connects the spider gear to the connection element, and the spider gear has a perpendicular orientation in relation to the two opposing gears.

18. The apparatus of claim 1, wherein the spider gear and the two opposing gears are conical or semi-spherical, have straight or helical teeth, and have a mechanism to prevent clearances or backlash.

19. The apparatus of claim 1, wherein the connection element which has the shape of a prism with polygonal or circular base, the shape of a sphere, or the shape of a polyhedron.

20. The apparatus of claim 1, further including a gear reduction box operatively coupling one of the two opposing gears and one of the two motors.

21. The apparatus of claim 1, wherein the motors have a torque between about 0.05 Nm and about 50 Nm, and position sensors are in electrical connection with the motors.

22. The apparatus of claim 1, wherein each motor is aligned axially with one of the opposing gears or is positioned perpendicularly to one of the opposing gears.

23. The apparatus of claim 1, wherein the drivers are configured to receive logical signals from the management and control system, convert the logical signals into electrical signals, and transmit the electrical signals to the motors.

24. The apparatus of claim 1, wherein the virtual or augmented reality software is configured to: display environments with figures, colors, and sounds to simulate a user's daily life situations; exhibit the user's movements; show corrections to the user's movement; and be used by one or more patients simultaneously.

25. The apparatus of claim 1, wherein the virtual or augmented reality software communicates with a database configured to store data about movements and exercises for motor rehabilitation or for training and physical fitness exercises.

26. The apparatus of claim 1, wherein the management and control system is configured to: calculate a trajectory, a force, and an acceleration for execution by the user in each movement; send logical signals to the drivers; receive feedback from the drivers; recalculate the trajectory, the force, and the acceleration of the user's movement based upon the feedback; send signals to the drivers for the correction of the user's movements; and send logical signals to the virtual or augmented reality software to show the corrections of movements on the display.

27. The apparatus of claim 1, further including at least one video port having a format of USB, VGA, HDMI, DVI, or other standard market format.

28. The apparatus of claim 1, further including a human interface device configured to access control interface functions.

29. The apparatus of claim 1, wherein the apparatus is sized for transportation by a single person and is configured for operation without external installations.

30. The apparatus of claim 1, further including virtual or augmented reality glasses for visualization of games, scenarios, and environments of the virtual or augmented reality software.

* * * * *